US010092649B2

(12) United States Patent
Smith et al.

(10) Patent No.: US 10,092,649 B2
(45) Date of Patent: Oct. 9, 2018

(54) 4'-DIFLUOROMETHYL SUBSTITUTED NUCLEOSIDE DERIVATIVES AS INHIBITORS OF INFLUENZA RNA REPLICATION

(71) Applicant: Riboscience LLC, Palo Alto, CA (US)

(72) Inventors: Mark Smith, San Francisco, CA (US); Klaus G. Klumpp, West Chester, PA (US)

(73) Assignee: Riboscience LLC, Palo Alto, CA (US)

( * ) Notice: Subject to any disclaimer, the term of this patent is extended or adjusted under 35 U.S.C. 154(b) by 0 days.

(21) Appl. No.: 15/187,014

(22) Filed: Jun. 20, 2016

(65) Prior Publication Data

US 2017/0296664 A1    Oct. 19, 2017

Related U.S. Application Data

(63) Continuation of application No. 14/615,928, filed on Feb. 6, 2015, now Pat. No. 9,370,569.

(60) Provisional application No. 61/936,569, filed on Feb. 6, 2014.

(51) Int. Cl.
| | |
|---|---|
| *C07H 7/06* | (2006.01) |
| *A61K 45/06* | (2006.01) |
| *C07H 19/06* | (2006.01) |
| *C07H 19/10* | (2006.01) |
| *A61K 31/7068* | (2006.01) |
| *C07H 19/16* | (2006.01) |
| *A61K 31/7076* | (2006.01) |
| *A61K 31/708* | (2006.01) |
| *C07H 19/213* | (2006.01) |
| *A61K 31/7072* | (2006.01) |

(52) U.S. Cl.
CPC ............ *A61K 45/06* (2013.01); *A61K 31/708* (2013.01); *A61K 31/7068* (2013.01); *A61K 31/7072* (2013.01); *A61K 31/7076* (2013.01); *C07H 7/06* (2013.01); *C07H 19/06* (2013.01); *C07H 19/10* (2013.01); *C07H 19/16* (2013.01); *C07H 19/213* (2013.01)

(58) Field of Classification Search
None
See application file for complete search history.

(56) References Cited

U.S. PATENT DOCUMENTS

| 5,192,749 | A | 3/1993 | O-Yang et al. |
| 7,105,499 | B2 | 9/2006 | Carroll et al. |
| 9,370,569 | B2 * | 6/2016 | Smith .................... C07H 19/06 |
| 2003/0087873 | A1 | 5/2003 | Stuyver et al. |
| 2004/0229840 | A1 | 11/2004 | Bhat et al. |
| 2010/0003213 | A1 | 1/2010 | Devos et al. |
| 2013/0165400 | A1 | 6/2013 | Beigelman et al. |
| 2013/0243725 | A1 | 9/2013 | Clarke |
| 2013/0315868 | A1 | 11/2013 | Mayes et al. |
| 2014/0178338 | A1 | 6/2014 | Mayes et al. |
| 2014/0179627 | A1 | 6/2014 | Beigelman et al. |
| 2014/0179910 | A1 | 6/2014 | Beigelman et al. |
| 2015/0011497 | A1 * | 1/2015 | Beigelman ............ C07H 19/11 |
| | | | 514/47 |
| 2015/0051167 | A1 | 2/2015 | Wang et al. |

FOREIGN PATENT DOCUMENTS

| WO | 2012037038 A1 | 3/2012 |
| WO | 2012040124 A1 | 3/2012 |
| WO | 2013096679 A1 | 6/2013 |
| WO | 2013138236 A1 | 9/2013 |
| WO | 2014100505 A1 | 6/2014 |
| WO | 2014209979 A1 | 12/2014 |
| WO | 2015054465 A1 | 4/2015 |

* cited by examiner

*Primary Examiner* — Traviss C McIntosh, III
(74) *Attorney, Agent, or Firm* — GrayRobinson, P.A.; Jennifer L. Kisko

(57) ABSTRACT

The application discloses nucleoside derivatives of Formula I as inhibitors of Influenza RNA replication. In particular, the application discloses the use of purine and pyrimidine nucleoside derivatives of Formula I as inhibitors of Influenza RNA replication and pharmaceutical compositions containing such compounds.

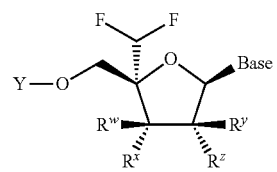

19 Claims, No Drawings

4'-DIFLUOROMETHYL SUBSTITUTED NUCLEOSIDE DERIVATIVES AS INHIBITORS OF INFLUENZA RNA REPLICATION

CROSS-REFERENCE TO RELATED APPLICATIONS

This application is a continuation application of U.S. Ser. No. 14/615,928, filed Feb. 6, 2015, and entitled "4'-Difluoromethyl Substituted Nucleoside Derivatives as Inhibitors of Influenza RNA Replication" which itself claims priority to application Ser. No. 61/936,569, filed Feb. 6, 2014. The contents of the co-pending applications are fully incorporated herein by reference.

FIELD OF THE INVENTION

The invention relates to nucleoside derivatives as inhibitors of Influenza RNA replication. In particular, the invention is concerned with the use of purine and pyrimidine nucleoside derivatives as inhibitors of Influenza RNA replication and pharmaceutical compositions containing such compounds.

Influenza virus is causing seasonal epidemics of respiratory disease throughout the world. Approved treatment options for Influenza infection fall into two classes, neuraminidase inhibitors (Oseltamivir, Zanamivir) and M2 inhibitors (Amantadine, Rimantadine). However, the yearly influenza epidemics are still associated with a significant number of excess deaths every year. The occurrence of yearly deaths due to influenza and pneumonia correlates with circulating influenza virus and with the relative pathogenicity of the particular circulating influenza strain. In addition, new virus strains for which little or no population resistance exists can emerge through gene reassortment with viruses from a large animal reservoir and cause pandemics, which are a serious global public health issue. The available treatments of influenza virus infection have limited efficacy because of widespread resistance (amantadine, rimantadine) or requirement for early start of treatment (neuraminidase inhibitors). In addition, naturally resistant viruses have emerged that are resistant to both classes of inhibitors.

Many of the drugs approved for the treatment of viral infections are nucleosides or nucleoside analogues and most of these nucleoside analogue drugs inhibit viral replication, following conversion to the corresponding triphosphates, through inhibition of the viral polymerase enzymes. The influenza virus polymerase is essential for viral replication, and its inhibition by nucleoside triphosphate analogs results in the shut-down of virus production. Only very few nucleoside analogs have been previously found that can inhibit the influenza virus polymerase.

Influenza virus belongs to the family of Orthomyxoviridae. It is an RNA virus with a segmented negative sense RNA genome. The synthesis of viral messenger RNA and of viral genomic RNA in infected cells is performed by the trimeric influenza virus polymerase. Three virus encoded polymerase subunits (PA, PB1, PB2) and a virus encoded single stranded RNA binding protein (NP) are necessary and sufficient to perform RNA replication.

SUMMARY OF THE INVENTION

The compounds of Formula I are useful for the treatment of diseases mediated by Influenza and for pharmaceutical compositions comprising such compounds.

The application provides a compound of Formula I

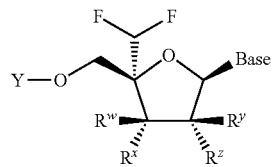

wherein:
Y is H or P(=X)(R')(R);
  R is O—$R^1$ or $NHR^{1'}$;
    $R^{1'}$ is —C($R^{2a}$)($R^{2b}$)C(=O)$OR^3$;
    $R^{1'}$ is N($R^4$)C($R^{2a}$)($R^{2b}$)C(=O)$OR^3$, —OP(=O)(OH)OP(=O)(OH)OH, or —$OR^3$;
      $R^1$ is H, lower haloalkyl, or aryl, wherein aryl is phenyl or naphthylenyl, optionally substituted with one or more lower alkyl, lower alkenyl, lower alkynyl, lower alkoxy, halo, lower haloalkyl, —N($R^{1a}$)$_2$, acylamino, —SO$_2$N($R^{1a}$)$_2$, —C(=O)$R^{1b}$, —SO$_2$($R^{1c}$), —NHSO$_2$($R^{1c}$), nitro, cyano, or $R^{1'''}$;
      each $R^{1a}$ is independently H or lower alkyl;
      each $R^{1b}$ is independently —$OR^{1a}$ or —N($R^{1a}$)$_2$;
      each $R^{1c}$ is lower alkyl;
      each $R^{2a}$ and $R^{2b}$ is independently H, lower alkyl, —(CH$_2$)$_r$N($R^{1a}$)$_2$, lower hydroxyalkyl, —CH$_2$SH, —(CH$_2$)S(O)$_p$Me, —(CH$_2$)$_n$NHC(=NH)NH$_2$, (1H-indol-3-yl)methyl, (1H-indol-4-yl)methyl, —(CH2)$_m$C(=O)$R^{1b}$, aryl and aryl lower alkyl, wherein aryl is optionally substituted with one or more hydroxy, lower alkyl, lower alkoxy, halo, nitro or cyano;
      m is 0, 1, or 2;
      n is 1, 2, or 3;
      p is 1 or 2;
      r is 1 or 2;
      or $R^{2a}$ is H and $R^{2b}$ and $R^4$ together form (CH$_2$)$_n$;
      each $R^3$ is independently H, lower alkyl, lower haloalkyl, phenyl or phenyl lower alkyl, wherein phenyl and phenyl lower alkyl are optionally substituted with lower alkoxy;
      or $R^3$ and $R^{1'''}$ together form CH$_2$;
each $R^4$ is independently H, lower alkyl;
or $R^{2b}$ and $R^4$ together form (CH$_2$)$_3$;
$R^w$, $R^y$, and $R^z$ are each independently H, OH or F;
$R^x$ is H, OH, or F;
or $R^3$ and $R^x$ together form a bond;
or $R^1$ and $R^x$ together form a bond;
X is O or S;
Base is uracil, cytosine, guanine, adenine, thymine, or heterocycloalkyl, each of which may optionally be substituted with one or more hydroxy, lower alkyl, lower alkoxy, halo, nitro or cyano;
with the proviso that if $R^w$ is H, $R^y$ is H, and $R^z$ is H, then $R^x$ is not H; and
with the proviso that Formula I is not ((2R,3R,4R,5R)-5-(4-amino-2-oxopyrimidin-1(2H)-yl)-2-(difluoromethyl)-4-fluoro-3-hydroxytetrahydrofuran-2-yl)methyl tetrahydrogen triphosphate; or a pharmacologically acceptable salt thereof.

The application provides the compounds of Formula I which are useful for the treatment of diseases mediated by Influenza, pharmaceutical compositions comprising such compounds of Formula I, or result in the formation of such compounds of Formula I in vivo during said treatment.

The application provides a method for treating an Influenza infection comprising administering to a patient in need thereof a therapeutically effective amount of a compound of Formula I or a compound resulting in the formation of a compound of Formula I in vivo.

the application provides a composition comprising a compound of Formula I and a pharmaceutically acceptable excipient.

DETAILED DESCRIPTION OF THE INVENTION

The compounds of Formula I have been shown to be inhibitors of the influenza virus RNA polymerase or result in the formation of inhibitors of the influenza virus polymerase after metabolic conversion in human cells.

The term "alkyl" as used herein denotes a straight or branched chain hydrocarbon residue containing 1 to 12 carbon atoms. Preferably, the term "alkyl" denotes a straight or branched chain hydrocarbon residue containing 1 to 7 carbon atoms. Most preferred are methyl, ethyl, propyl, isopropyl, n-butyl, isobutyl, tart.-butyl or plenty. The alkyl may be unsubstituted or substituted. The substituents are selected from one or more of cycloalkyl, nitro, amino, alkyl amino, dialkyl amino, alkyl carbonyl and cycloalkyl carbonyl.

The term "cycloalkyl" as used herein denotes an optionally substituted cycloalkyl group containing 3 to 7 carbon atoms, e.g. cyclopropyl, cyclobutyl, cyclopentyl, cyclohexyl or cycloheptyl.

The term "alkoxy" as used herein denotes an optionally substituted straight or branched chain alkyl-oxy group wherein the "alkyl" portion is as defined above such as methoxy, ethoxy, n-propyloxy, i-propyloxy, n-butyloxy, i-butyloxy, tert.-butyloxy, pentyloxy, hexyloxy, heptyloxy including their isomers.

The term "alkoxyalkyl" as used herein denotes an alkoxy group as defined above which is bonded to an alkyl group as defined above. Examples are methoxymethyl, methoxyethyl, methoxypropyl, ethoxymethyl, ethoxyethyl, ethoxypropyl, propyloxypropyl, methoxybutyl, ethoxybutyl, propyloxybutyl, butyloxybutyl, tert.-butyloxybutyl, methoxypentyl, ethoxypentyl, propyloxypentyl including their isomers.

The term "alkenyl" as used herein denotes an unsubstituted or substituted hydrocarbon chain radical having from 2 to 7 carbon atoms, preferably from 2 to 4 carbon atoms, and having one or two olefinic double bonds, preferably one olefinic double bond. Examples are vinyl, 1-propenyl, 2-propenyl (allyl) or 2-butenyl (crotyl).

The term "alkynyl" as used herein denotes to unsubstituted or substituted hydrocarbon chain radical having from 2 to 7 carbon atoms, preferably 2 to 4 carbon atoms, and having one or where possible two triple bonds, preferably one triple bond. Examples are ethynyl, 1-propynyl, 2-propynyl, 1-butynyl, 2-butynyl or 3-butynyl.

The term "H" as used herein refers to hydrogen, including deuterium.

The term "hydroxyalkyl" as used herein denotes a straight or branched chain alkyl group as defined above wherein 1, 2, 3 or more hydrogen atoms are substituted by a hydroxy group. Examples are hydroxymethyl, 1-hydroxyethyl, 2-hydroxyethyl, 1-hydroxypropyl, 2-hydroxypropyl, 3-hydroxypropyl, hydroxyisopropyl, hydroxybutyl and the like.

The term "haloalkyl" as used herein denotes a straight or branched chain alkyl group as defined above wherein 1, 2, 3 or more hydrogen atoms are substituted by a halogen. Examples are 1-fluoromethyl, 1-chloromethyl, 1-bromomethyl, 1-iodomethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl and the like.

The term "alkylthio" as used herein denotes a straight or branched chain (alkyl)S-group wherein the "alkyl" portion is as defined above. Examples are methylthio, ethylthio, n-propylthio, i-propylthio, n-butylthio, i-butylthio or tert.-butylthio.

The term "aryl" as used herein denotes an optionally substituted phenyl and naphthyl (also referred to as naphthylenyl") (e.g. 1-naphthyl, 2-naphthyl or 3-naphthyl). Suitable substituents for aryl can be selected from those named for alkyl, in addition however, halogen, hydroxy and optionally substituted alkyl, haloalkyl, alkenyl, alkynyl and aryloxy are substituents which can be added to the selection.

The term "heterocyclyl" or "heterocycloalkyl" or "heterocycle" as used herein denotes an optionally substituted saturated, partially unsaturated or aromatic monocyclic, bicyclic or tricyclic heterocyclic systems which contain one or more hetero atoms selected from nitrogen, oxygen and sulfur which can also be fused to an optionally substituted saturated, partially unsaturated or aromatic monocyclic carbocycle or heterocycle.

Examples of suitable heterocycles are oxazolyl, isoxazolyl, furyl, tetrahydrofuryl, 1,3-dioxolanyl, dihydropyranyl, 2-thienyl, 3-thienyl, pyrazinyl, isothiazolyl, dihydrooxazolyl, pyrimidinyl, tetrazolyl, 1-pyrrolidinyl, 2-pyrrolidinyl, 3-pyrrolidinyl, pyrrolidinonyl, (N-oxide)-pyridinyl, 1-pyrrolyl, 2-pyrrolyl, triazolyl e.g. 1,2,3-triazolyl or 1,2,4-triazolyl, 1-pyrazolyl, 2-pyrazolyl, 4-pyrazolyl, piperidinyl, morpholinyl (e.g. 4-morpholinyl), thiomorpholinyl (e.g. 4-thiomorpholinyl), thiazolyl, pyridinyl, dihydrothiazolyl, imidazolidinyl, pyrazolinyl, piperazinyl, 1-imidazolyl, 2-imidazolyl, 4-imidazolyl, thiadiazolyl e.g. 1,2,3-thiadiazolyl, 4-methylpiperazinyl, 4-hydroxypiperidin-1-yl.

Suitable substituents for heterocycloalkyls can be selected from those named for alkyl, in addition however, optionally substituted alkyl, alkenyl, alkynyl, an oxo group (=O) or aminosulphonyl are substituents which can be added to the selection.

The term "acyl" ("alkylcarbonyl") as used herein denotes a group of formula C(=O)R wherein R is hydrogen, an unsubstituted or substituted straight or branched chain hydrocarbon residue containing 1 to 7 carbon atoms or a phenyl group. Most preferred acyl groups are those wherein R is hydrogen, an unsubstituted straight chain or branched hydrocarbon residue containing 1 to 4 carbon atoms or a phenyl group.

The term "halogen" or "halo" stands for fluorine, chlorine, bromine or iodine, preferable fluorine, chlorine, bromine.

In the pictorial representation of the compounds given throughout this application, a thickened tapered line (▬▬▬) indicates a substituent which is above the plane of the ring to which the asymmetric carbon belongs and a dotted line (▫▫▫▫▫) indicates a substituent which is below the plane of the ring to which the asymmetric carbon belongs.

Compounds of formula I may exhibit stereoisomerism. These compounds can be any isomer of the compound of formula I or mixtures of these isomers. The compounds and intermediates of the present invention having one or more asymmetric carbon atoms may be obtained as racemic mixtures of stereoisomers which can be resolved.

Compounds of formula I may exhibit tautomerism which means that the compounds of this invention can exist as two or more chemical compounds that are capable of facile interconversion. In many cases it merely means the exchange of a hydrogen atom between two other atoms, to either of which it forms a covalent bond. Tautomeric compounds exist in a mobile equilibrium with each other, so that attempts to prepare the separate substances usually result in the formation of a mixture that shows all the chemical and physical properties to be expected on the basis of the structures of the components.

The most common type of tautomerism is that involving carbonyl, or keto, compounds and unsaturated hydroxyl compounds, or enols. The structural change is the shift of a hydrogen atom between atoms of carbon and oxygen, with the rearrangement of bonds. For example, in many aliphatic aldehydes and ketones, such as acetaldehyde, the keto form is the predominant one; in phenols, the enol form is the major component.

Compounds of formula I which are basic can form pharmaceutically acceptable salts with inorganic acids such as hydrohalic acids (e.g. hydrochloric acid and hydrobromic acid), sulphuric acid, nitric acid and phosphoric acid, and the like, and with organic acids (e.g. with acetic acid, tartaric acid, succinic acid, fumaric acid, maleic acid, malic acid, salicylic acid, citric acid, methanesulphonic acid and p-toluene sulphonic acid, and the like). The formation and isolation of such salts can be carried out according to methods known in the art.

Inhibitors of Influenza

The application provides a compound of Formula I

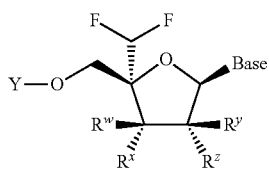

I wherein:
Y is H or P(=X)(R')(R);
  R is O—$R^1$ or $NHR^{1"}$;
    $R^{1'}$ is —$C(R^{2a})(R^{2b})C(=O)OR^3$;
  R' is $N(R^4)C(R^{2a})(R^{2b})C(=O)OR^3$, —OP(=O)(OH)OP(=O)(OH)OH, or —$OR^3$;
    $R^1$ is H, lower haloalkyl, or aryl, wherein aryl is phenyl or naphthylenyl, optionally substituted with one or more lower alkyl, lower alkenyl, lower alkynyl, lower alkoxy, halo, lower haloalkyl, —$N(R^{1a})_2$, acylamino, —$SO_2N(R^{1a})_2$, —$C(=O)R^{1b}$, —$SO_2(R^{1c})$, —$NHSO_2(R^{1c})$, nitro, cyano, or $R^{1"}$;
    each $R^{1a}$ is independently H or lower alkyl;
    each $R^{1b}$ is independently —$OR^{1a}$ or —$N(R^{1a})_2$;
    each $R^{1c}$ is lower alkyl;
    each $R^{2a}$ and $R^{2b}$ is independently H, lower alkyl, —$(CH_2)_rN(R^{1a})_2$, lower hydroxyalkyl, —$CH_2SH$, —$(CH_2)S(O)_pMe$, —$(CH_2)_nNHC(=NH)NH_2$, (1H-indol-3-yl)methyl, (1H-indol-4-yl)methyl, —$(CH2)_mC(=O)R^{1b}$, aryl and aryl lower alkyl, wherein aryl is optionally substituted with one or more hydroxy, lower alkyl, lower alkoxy, halo, nitro or cyano;

m is 0, 1, or 2;
n is 1, 2, or 3;
p is 1 or 2;
r is 1 or 2;
or $R^{2a}$ is H and $R^{2b}$ and $R^4$ together form $(CH_2)_n$;
each $R^3$ is independently H, lower alkyl, lower haloalkyl, phenyl or phenyl lower alkyl, wherein phenyl and phenyl lower alkyl are optionally substituted with lower alkoxy;
or $R^3$ and $R^{1"}$ together form $CH_2$;
each $R^4$ is independently H, lower alkyl;
or $R^{2b}$ and $R^4$ together form $(CH_2)_3$;
$R^w$, $R^y$, and $R^z$ are each independently H, OH or F;
$R^x$ is H, OH, or F;
or $R^3$ and $R^x$ together form a bond;
or $R^1$ and $R^x$ together form a bond;
X is O or S;
Base is uracil, cytosine, guanine, adenine, thymine, or heterocycloalkyl, each of which may optionally be substituted with one or more hydroxy, lower alkyl, lower alkoxy, halo, nitro or cyano;
with the proviso that if $R^w$ is H, $R^y$ is H, and $R^z$ is H, then $R^x$ is not H; and
with the proviso that Formula I is not ((2R,3R,4R,5R)-5-(4-amino-2-oxopyrimidin-1(2H)-yl)-2-(difluoromethyl)-4-fluoro-3-hydroxytetrahydrofuran-2-yl)methyl tetrahydrogen triphosphate;
or a pharmacologically acceptable salt thereof.

The application provides the above compound of Formula I, wherein $R^w$ is H, $R^y$ is H, $R^x$ is OH, and $R^z$ is OH.

The application alternatively provides the above compound of Formula I, wherein $R^w$ is F, $R^y$ is H, $R^x$ is F, and $R^z$ is OH.

The application alternatively provides the above compound of Formula I, wherein $R^w$ is OH, $R^y$ is H, $R^x$ is H, and $R^z$ is OH.

The application alternatively provides the above compound of Formula I, wherein $R^w$ is F, $R^y$ is H, $R^x$ is H, and $R^z$ is OH.

The application alternatively provides the above compound of Formula I, wherein $R^w$ is H, $R^y$ is H, $R^x$ is F, and $R^z$ is OH.

The application alternatively provides the above compound of Formula I, wherein $R^w$ is H, $R^y$ is OH, $R^x$ is OH, and $R^z$ is H.

The application alternatively provides the above compound of Formula I, wherein $R^w$ is H, $R^y$ is F, $R^x$ is OH, and $R^z$ is F.

The application alternatively provides the above compound of Formula I, wherein $R^w$ is H, $R^y$ is F, $R^x$ is OH, and $R^z$ is H.

The application alternatively provides the above compound of Formula I, wherein $R^w$ is H, $R^y$ is H, $R^x$ is OH, and $R^z$ is F.

The application provides the compound of Formula I, wherein $R^z$ is H.

The application provides the compound of Formula I, wherein $R^y$ is OH.

The application provides the compound of Formula I, wherein $R^w$ is H.

The application provides the compound of Formula I, wherein $R^x$ is OH.

The application provides the compound of Formula I, wherein R' is O—$R^3$, $R^3$ is lower alkyl, R is —$OR^1$, and $R^1$ and $R^x$ together form a bond.

The application provides the compound of Formula I, wherein R is —OR$^1$, R$^1$ is phenyl substituted with R$^{1'''}$, R' is —OR$^3$, and R$^3$ and R$^{1'''}$ together form CH$_2$.

The application provides the compound of Formula I, wherein X is O.

The application provides the compound of Formula I, wherein X is S.

The application provides the compound of Formula I, wherein R is O—R$^1$, and R$^1$ is phenyl optionally substituted with methoxy.

The application provides the compound of Formula I, wherein R is O—R$^1$, and R$^1$ is naphthylenyl.

The application provides the compound of Formula I, wherein R' is N(R$^4$)C(R$^{2a}$)(R$^{2b}$)C(=O)OR$^3$, R$^4$ is H, R$^{2a}$ is H, R$^{2b}$ is methyl, and R$^3$ is isopropyl.

The application provides the compound of Formula I, wherein R' is —OP(=O)(OH)OP(=O)(OH)OH.

The application provides the compound of Formula I, wherein Base is cytidine optionally substituted with halo.

The application provides the compound of Formula I, wherein Base is uridine optionally substituted with halo.

The application provides the compound of Formula I, wherein Base is guanosine.

The application provides the compound of Formula I, wherein Base is adenosine.

The application provides the compound of Formula I, wherein R$^w$ is F if R$^w$ is not H or OH.

The application provides the compound of Formula I, wherein R$^y$ is F if R$^y$ is not H or OH.

The application provides the compound of Formula I, wherein R$^z$ is F if R$^z$ is not H or OH.

The application provides the compound of Formula I, wherein both R$^y$ and R$^z$ are F if both R$^y$ and R$^z$ are not H or OH.

The application provides the compound of Formula I, wherein R$^y$ is H and R$^z$ is OH if R$^y$ is not OH or F and R$^z$ is not H or F.

The application provides a composition comprising the compound of Formula I.

The application provides the above composition, admixed with at least one carrier, diluent or excipient.

The application provides a composition comprising the compound of Formula I in combination with one or more antiviral compounds.

The application provides a composition comprising the compound of Formula I in combination with one or more anti-Influenza compounds.

The application provides a composition comprising the compound of Formula I in combination with one or more antiviral compounds, admixed with at least one carrier, diluent or excipient.

The application provides a composition comprising the compound of Formula I in combination with one or more anti-Influenza compounds, admixed with at least one carrier, diluent or excipient.

The application provides a method of preventing or treating a virus comprising administering to a patient in need thereof a therapeutically effective amount of the compound of Formula I.

The application provides a method for treating an Influenza infection comprising administering to a patient in need thereof a therapeutically effective amount of a compound of Formula I, or a compound resulting in the formation of a compound of Formula I in vivo,

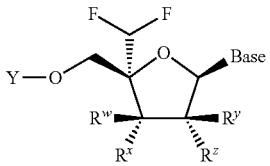

I wherein:
Y is H or P(=X)(R')(R);
R is O—R$^1$ or NHR$^{1'}$;
R$^{1'}$ is —C(R$^{2a}$)(R$^{2b}$)C(=O)OR$^3$;
R' is N(R$^4$)C(R$^{2a}$)(R$^{2b}$)C(=O)OR$^3$, —OP(=O)(OH)OP(=O)(OH)OH, or —OR$^3$;
  R$^1$ is H, lower haloalkyl, or aryl, wherein aryl is phenyl or naphthylenyl, optionally substituted with one or more lower alkyl, lower alkenyl, lower alkynyl, lower alkoxy, halo, lower haloalkyl, —N(R$^{1a}$)$_2$, acylamino, —SO$_2$N(R$^{1a}$)$_2$, —C(=O)R$^b$, —SO$_2$(R$^{1c}$), —NHSO$_2$(R$^{1c}$), nitro, cyano, or R$^{1''}$;
  each R$^{1a}$ is independently H or lower alkyl;
  each R$^{1b}$ is independently —OR$^{1a}$ or —N(R$^{1a}$)$_2$;
  each R$^{1c}$ is lower alkyl;
  each R$^{2a}$ and R$^{2b}$ is independently H, lower alkyl, —(CH$_2$)$_r$N(R$^{1a}$)$_2$, lower hydroxyalkyl, —CH$_2$SH, —(CH$_2$)S(O)$_p$Me, —(CH$_2$)$_n$NHC(=NH)NH$_2$, (1H-indol-3-yl)methyl, (1H-indol-4-yl)methyl, —(CH2)$_m$C(=O)R$^{1b}$, aryl and aryl lower alkyl, wherein aryl is optionally substituted with one or more hydroxy, lower alkyl, lower alkoxy, halo, nitro or cyano;
  m is 0, 1, or 2;
  n is 1, 2, or 3;
  p is 1 or 2;
  r is 1 or 2;
  or R$^{2a}$ is H and R$^{2b}$ and R$^4$ together form (CH$_2$)$_n$;
  each R$^3$ is independently H, lower alkyl, lower haloalkyl, phenyl or phenyl lower alkyl, wherein phenyl and phenyl lower alkyl are optionally substituted with lower alkoxy;
  or R$^3$ and R$^{1'''}$ together form CH$_2$;
each R$^4$ is independently H, lower alkyl;
or R$^{2b}$ and R$^4$ together form (CH$_2$)$_3$;
R$^w$, R$^y$, and R$^z$ are each independently H, OH or F;
R$^x$ is H, OH, or F;
or R$^3$ and R$^x$ together form a bond;
or R$^1$ and R$^x$ together form a bond;
X is O or S;
Base is uracil, cytosine, guanine, adenine, thymine, or heterocycloalkyl, each of which may optionally be substituted with one or more hydroxy, lower alkyl, lower alkoxy, halo, nitro or cyano; and
with the proviso that if R$^w$ is H, R$^y$ is H, and R$^z$ is H, then R$^x$ is not H;
or a pharmacologically acceptable salt thereof.

The application provides a method for treating an Influenza infection comprising administering to a patient in need thereof a therapeutically effective amount of a compound of Formula I, or a compound resulting in the formation of a compound of Formula I in vivo,

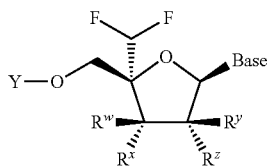

I wherein:
Y is H or P(=X)(R')(R);
  R is O—R$^1$ or NHR$^{1'}$;
    R$^{1'}$ is —C(R$^{2a}$)(R$^{2b}$)C(=O)OR$^3$;
  R' is N(R$^4$)C(R$^{2a}$)(R$^{2b}$)C(=O)OR$^3$, —OP(=O)(OH)OP(=O)(OH)OH, or —OR$^3$;
    R$^1$ is H, lower haloalkyl, or aryl, wherein aryl is phenyl or naphthylenyl, optionally substituted with one or more lower alkyl, lower alkenyl, lower alkynyl, lower alkoxy, halo, lower haloalkyl, —N(R$^{1a}$)$_2$, acylamino, —SO$_2$N(R$^{1a}$)$_2$, —C(=O)R$^{1b}$, —SO$_2$(R$^{1c}$), —NHSO$_2$(R$^{1c}$), nitro, cyano, or R$^{1''}$;
    each R$^{1a}$ is independently H or lower alkyl;
    each R$^{1b}$ is independently —OR$^{1a}$ or —N(R$^{1a}$)$_2$;
    each R$^{1c}$ is lower alkyl;
    each R$^{2a}$ and R$^{2b}$ is independently H, lower alkyl, —(CH$_2$)$_r$N(R$^{1a}$)$_2$, lower hydroxyalkyl, —CH$_2$SH, —(CH$_2$)S(O)$_p$Me, —(CH$_2$)$_n$NHC(=NH)NH$_2$, (1H-indol-3-yl)methyl, (1H-indol-4-yl)methyl, —(CH2)$_m$C(=O)R$^{1b}$, aryl and aryl lower alkyl, wherein aryl is optionally substituted with one or more hydroxy, lower alkyl, lower alkoxy, halo, nitro or cyano;
    m is 0, 1, or 2;
    n is 1, 2, or 3;
    p is 1 or 2;
    r is 1 or 2;
    or R$^{2a}$ is H and R$^{2b}$ and R$^4$ together form (CH$_2$)$_n$;
    each R$^3$ is independently H, lower alkyl, lower haloalkyl, phenyl or phenyl lower alkyl, wherein phenyl and phenyl lower alkyl are optionally substituted with lower alkoxy;
    or R$^3$ and R$^{1''}$ together form CH$_2$;
  each R$^4$ is independently H, lower alkyl;
  or R$^{2b}$ and R$^4$ together form (CH$_2$)$_3$;
  R$^w$, R$^y$, and R$^z$ are each independently H, OH or F;
  R$^x$ is H, OH, or F;
  or R$^3$ and R$^x$ together form a bond;
  or R$^1$ and R$^x$ together form a bond;
  X is O or S; and
Base is uracil, cytosine, guanine, adenine, thymine, or heterocycloalkyl, each of which may optionally be substituted with one or more hydroxy, lower alkyl, lower alkoxy, halo, nitro or cyano;
or a pharmacologically acceptable salt thereof.

The application provides a method for preventing or treating an Influenza infection comprising administering to a patient in need thereof a therapeutically effective amount of a compound of Formula I or a compound resulting in the formation of a compound of Formula I in vivo.

The application provides the use of a compound of Formula I in the preparation of a medicament for the treatment of a viral infection.

The application provides the use of the compound of Formula I in the preparation of a medicament for the treatment of an Influenza infection.

The application provides any compound, composition, method, or use as described herein.

The application provides the above method, further comprising administering an immune system modulator or one or more antiviral agents that inhibits replication of Influenza, or a combination thereof.

The application provides the above method for inhibiting replication of Influenza in a cell comprising administering a compound of Formula I.

Examples of representative compounds encompassed by the present invention and within the scope of the invention are provided in the following Tables. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on standard nucleic acid nomenclature common to one of ordinary skill in the art. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

EXAMPLES

Abbreviations used in this application include: acetyl (Ac), acetic acid (HOAc), azo-bis-isobutyrylnitrile (AIBN), 1-N-hydroxybenzotriazole (HOBt), atmospheres (Atm), high pressure liquid chromatography (HPLC), 9-borabicyclo[3.3.1]nonane (9-BBN or BBN), methyl (Me), tert-butoxycarbonyl (Boc), acetonitrile (MeCN), di-tert-butyl pyrocarbonate or boc anhydride (BOC$_2$O), 1-(3-dimethylaminopropyl)-3-ethylcarbodiimide hydrochloride (EDCI), benzoyl (Bz), benzyl (Bn), m-chloroperbenzoic acid (MCPBA), butyl (Bu), methanol (MeOH), benzyloxycarbonyl (cbz or Z), melting point (mp), carbonyl diimidazole (CDI), MeSO$_2$— (mesyl or Ms), 1,4-diazabicyclo[2.2.2]octane (DABCO), mass spectrum (ms) diethylaminosulfur trifluoride (DAST), methyl t-butyl ether (MTBE), dibenzylideneacetone (Dba), N-carboxyanhydride (NCA), 1,5-diazabicyclo[4.3.0]non-5-ene (DBN), N-bromosuccinimide (NBS), 1,8-diazabicyclo[5.4.0]undec-7-ene (DBU), N-methylmorpholine (NMM), N-methylpyrrolidone (NMP), 1,2-dichloroethane (DCE), pyridinium chlorochromate (PCC), N,N'-dicyclohexylcarbodiimide (DCC), pyridinium dichromate (PDC), dichloromethane (DCM), propyl (Pr), diethyl azodicarboxylate (DEAD), phenyl (Ph), di-iso-propylazodicarboxylate, DIAD, pounds per square inch (psi), di-iso-propylethylamine (DIPEA), pyridine (pyr), di-iso-butylaluminumhydride, DIBAL-H, room temperature, rt or RT, N,N-dimethyl acetamide (DMA), tert-butyldimethylsilyl or t-BuMe$_2$Si, (TBDMS), 4-N,N-dimethylaminopyridine (DMAP), triethylamine (Et$_3$N or TEA), N,N-dimethylformamide (DMF), triflate or CF$_3$SO$_2$-(Tf), dimethyl sulfoxide (DMSO), trifluoroacetic acid (TFA), 1,1'-bis-(diphenylphosphino)ethane (dppe), 2,2,6,6-tetramethylheptane-2,6-dione (TMHD), 1,1'-bis-(diphenylphosphino)ferrocene (dppf), thin layer chromatography (TLC), ethyl acetate (EtOAc), tetrahydrofuran (THF), diethyl ether (Et$_2$O), trimethylsilyl or Me$_3$Si (TMS), ethyl (Et), p-toluenesulfonic acid monohydrate (TsOH or pTsOH), lithium hexamethyl disilazane (LiHMDS), 4-Me-C$_6$H$_4$SO$_2$— or tosyl (Ts), iso-propyl (i-Pr), N-urethane-N-carboxyanhydride (UNCA), ethanol (EtOH). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

General Conditions

Compounds of the invention can be made by a variety of methods depicted in the illustrative synthetic reactions described below in the Examples section.

The starting materials and reagents used in preparing these compounds generally are either available from commercial suppliers, such as Aldrich Chemical Co., or are prepared by methods known to those skilled in the art following procedures set forth in references such as Fieser and Fieser's *Reagents for Organic Synthesis*; Wiley & Sons: New York, 1991, Volumes 1-15; Rodd's *Chemistry of Carbon Compounds*, Elsevier Science Publishers, 1989, Volumes 1-5 and Supplementals; and *Organic Reactions*, Wiley & Sons: New York, 1991, Volumes 1-40. It should be appreciated that the synthetic reaction schemes shown in the Examples section are merely illustrative of some methods by which the compounds of the invention can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein are typically conducted under an inert atmosphere at atmospheric pressure at a reaction temperature range of from about −78° C. to about 150° C., often from about 0° C. to about 125° C., and more often and conveniently at about room (or ambient) temperature, e.g., about 20° C.

Various substituents on the compounds of the invention can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups are known in the art, and can be employed. Examples of many of the possible groups can be found in "*Protective Groups in Organic Synthesis*" by Green et al., John Wiley and Sons, 1999. For example, nitro groups can be added by nitration and the nitro group can be converted to other groups, such as amino by reduction, and halogen by diazotization of the amino group and replacement of the diazo group with halogen. Acyl groups can be added by Friedel-Crafts acylation. The acyl groups can then be transformed to the corresponding alkyl groups by various methods, including the Wolff-Kishner reduction and Clemmenson reduction. Amino groups can be alkylated to form mono- and di-alkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product, including isolated products.

The starting material 1 can be purchased through numerous vendors (CAS: 63593-03-3). Selective benzyl protection followed by oxidation, under Swern conditions, provided aldehyde intermediate 3. Fluorination with DAST, followed by treatment with acetic anhydride under acidic conditions provided the diacetate intermediate 5. Vorbrüggen reaction followed by deprotection, under standard conditions, provided 4'-difluoromethyluridine 7 (Scheme 1).

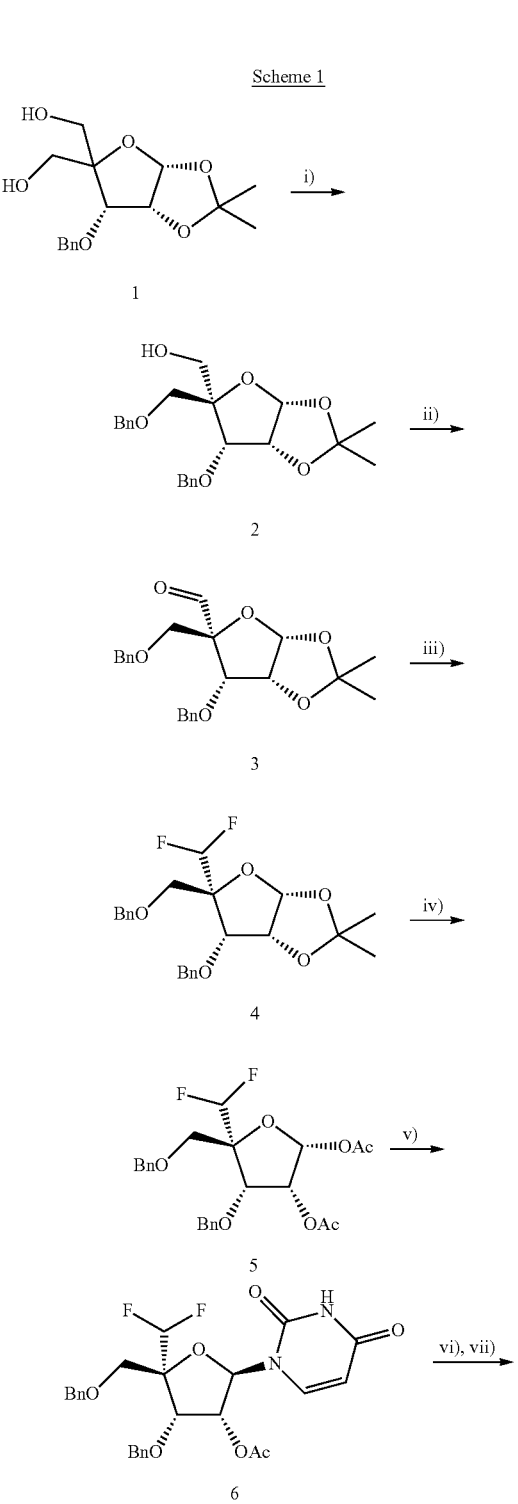

Scheme 1

13

-continued

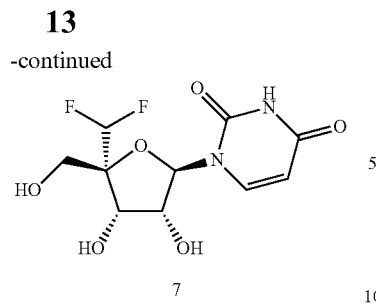
7 i) NaH, BnBr, DMF; ii) DMSO, (ClCO)₂, -78° C., iii) DAST, CH₂Cl₂; iv) Ac₂O, cat. H₂SO₄, AcOH; v) Uridine, BSA, SnCl₄, MeCN; vi) NH₃·H₂O, MeCN; vii) Pd(OH)₂/C, cat. HCl.

Compound 8 can be prepared, from the uridine analogue 7, by those skilled in the art of organic synthesis following the synthetic sequence outlined below (Scheme 2).

Scheme 2

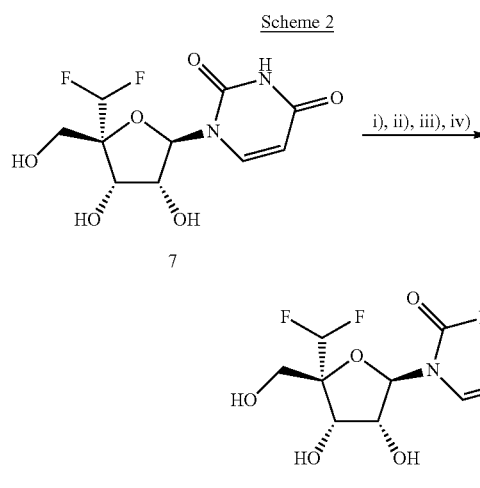

i) Ac₂O, AcOH; ii) 4-Cl—CPhOP(O)Cl₂, 1-H-tetrazole, pyridine; iii) NH₃, H₂O; iv) NH₃, MeOH Phosphoramidate compounds of the present invention can be prepared by condensation of nucleoside 7, 8 or 9 with a suitably substituted phosphochloridate, or its sulfur analogue, of type 10 in the presence of a strong base (Scheme 3). The coupled product 11 of formula I is obtained as a mixture of two diastereomers initially under the coupling reaction and can be separated into their corresponding chiral enantiomers by chiral column, chiral HPLC, or chiral SFC chromatography.

Scheme 3

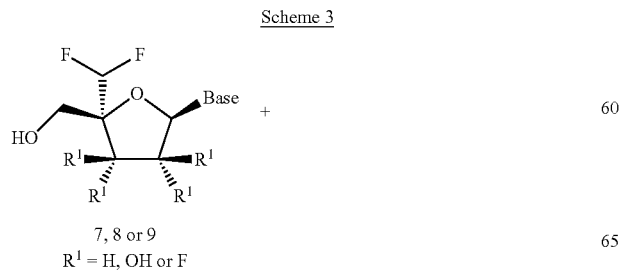

7, 8 or 9
R¹ = H, OH or F

14

-continued

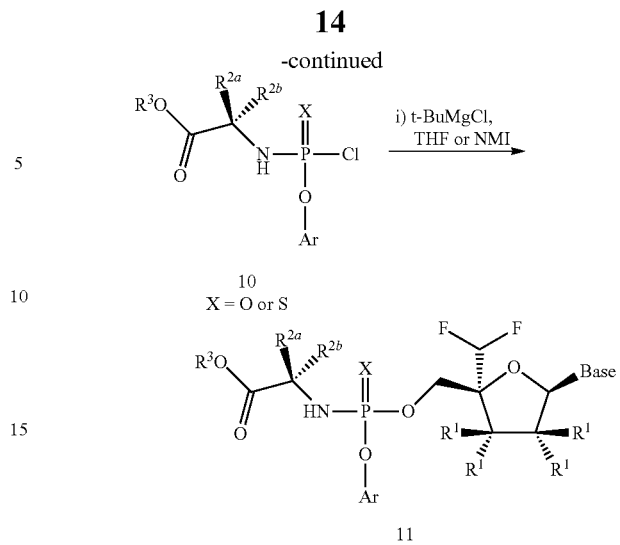

10
X = O or S

11

Phosphorodiamidate compounds of formula I in the present invention can be prepared by condensation of nucleoside 7, 8 or 9 with a suitably substituted phosphorodiamidic chloride, or phosphorodiamidothioic chloride, of type 12 in the presence of a strong base (Scheme 4).

Scheme 4

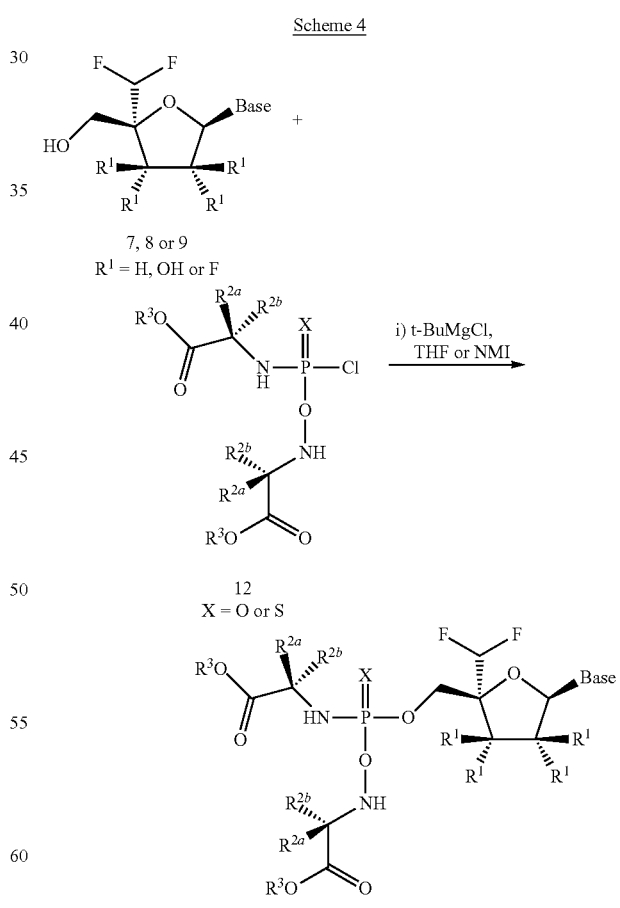

12
X = O or S

13

Cyclic phosphates of the present invention can be prepared by condensation of nucleoside 4 or 5 with isopropyl N,N,N,N-tetraisopropylphosphorodiamidite 14 (Scheme 5). Conversion to the thio derivative can be performed by heating the crude reaction mixture with bis(3-triethoxylsilyl)propyl-tetrasulfide (TEST).

Scheme 5

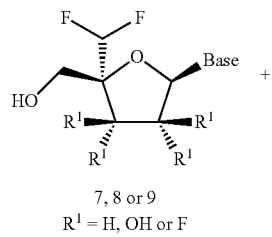

7, 8 or 9
$R^1$ = H, OH or F

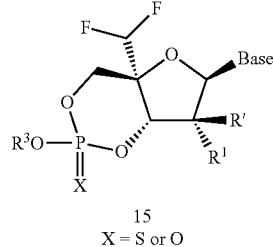

14 i) MeCN
ii) TEST or t-BuOOH

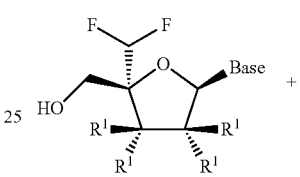

15
X = S or O

An alternative cyclic phosphate can be furnished from the reaction of the nucleoside 7, 8 or 9 with the appropriate chlorophosphite 16 in the presence of a base and Oxone (Scheme 6).

Scheme 6

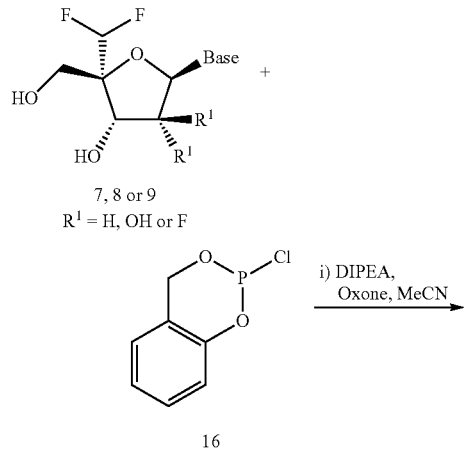

7, 8 or 9
$R^1$ = H, OH or F i) DIPEA, Oxone, MeCN

16

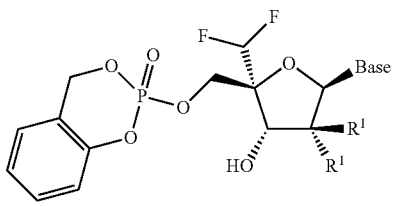

17

Phosphate prodrugs of type 19 are readily prepared from the reaction of compounds 7, 8 or 9 with chlorophosphates of type 18 (Scheme 7).

Scheme 7

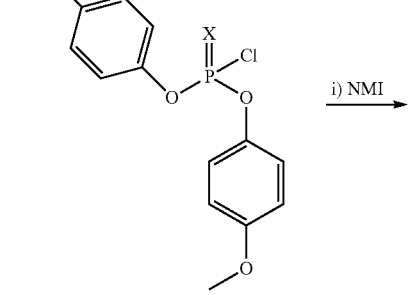

7, 8 or 9
$R^1$ = H, OH or F i) NMI

18

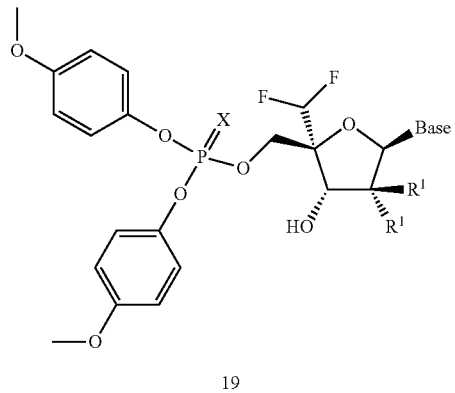

19

The synthesis of 4'-difluoromethylguanidine is outlined in Scheme 8. Herein, the ribose intermediate 5 undergoes a Vorbrüggen reaction with 20 to give the guanidine 23 derivative, following deprotection.

Scheme 8

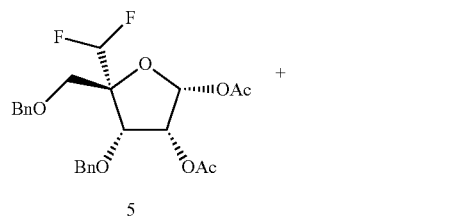
5

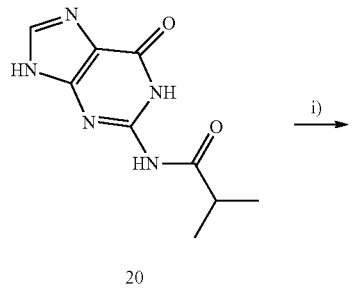
20

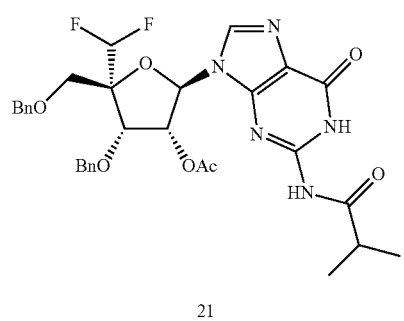
21

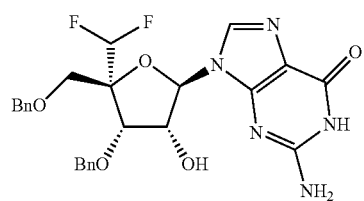
22

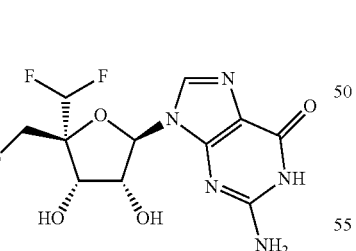
23 i) BSA, TMSOTf, MeCN; vi) NH₃·H₂O, MeCN; vii) HCOONH₄, MeOH

The synthesis of 4'-difluoromethyladenosine is outlined in Scheme 9. Herein, the ribose intermediate 5 undergoes a Vorbrüggen reaction with 24 to give the adenosine derivative 27, following deprotection.

Scheme 9

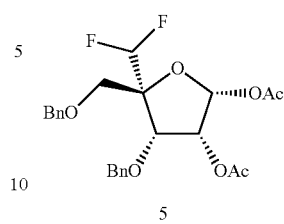
5

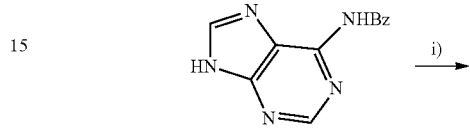
24

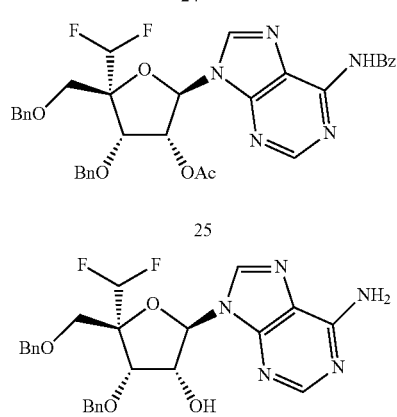

i) BSA, SnCl₄MeCN; vi) NH₃·H₂O, MeCN; vii) Pd(OH)₂/C, MeOH

Synthesis of 4'-difluoromethyl-5-chlorocytidine is outlined in Scheme 10. Herein, the ribose intermediate 5 undergoes a Vorbrüggen reaction with 28 to give the cytidine derivative 31, following deprotection.

Scheme 10

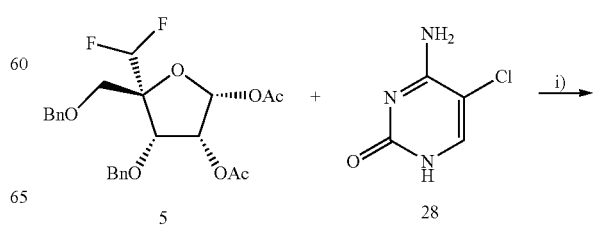

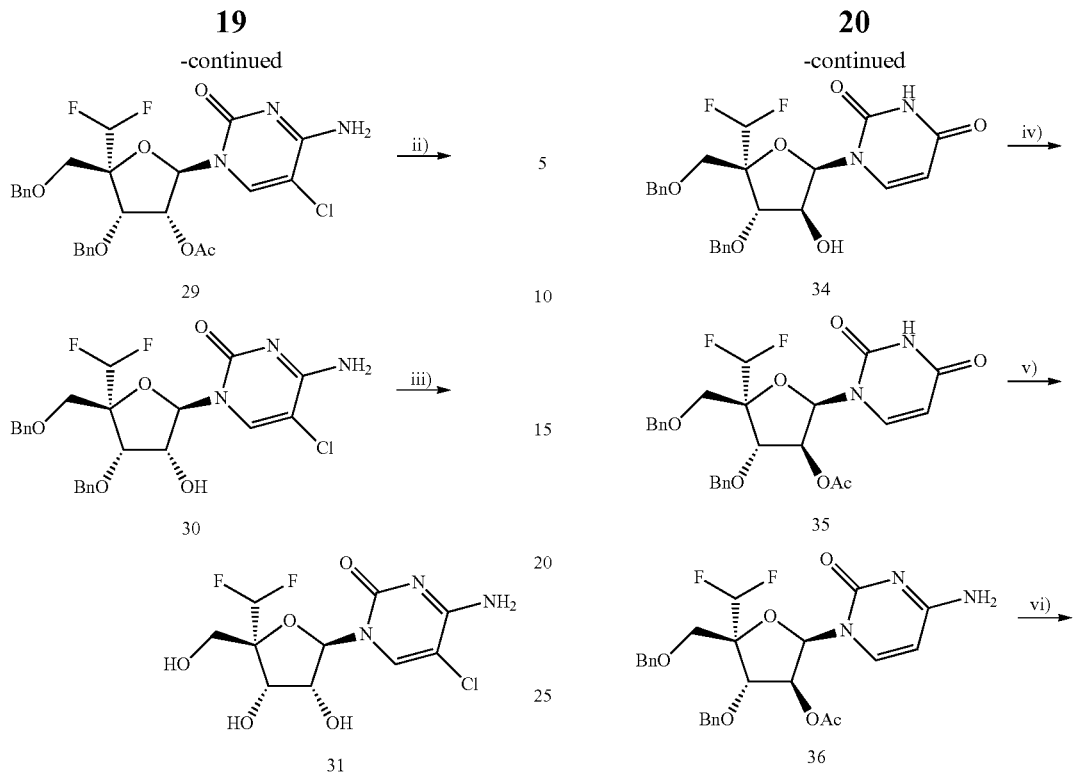

i) BSA, SnCl₄MeCN; ii) NH₃, MeOH; iii) BCl₃, CH₂Cl₂, -78° C.

4'-Difluoromethylaracytidine synthesis is outlined in Scheme 11. Herein, the uridine intermediate 6 is reacted with diphenyl carbonate to provide the anhydro compound 33. Hydrolysis and deprotection yield the arabinocytidine 38, following deprotection.

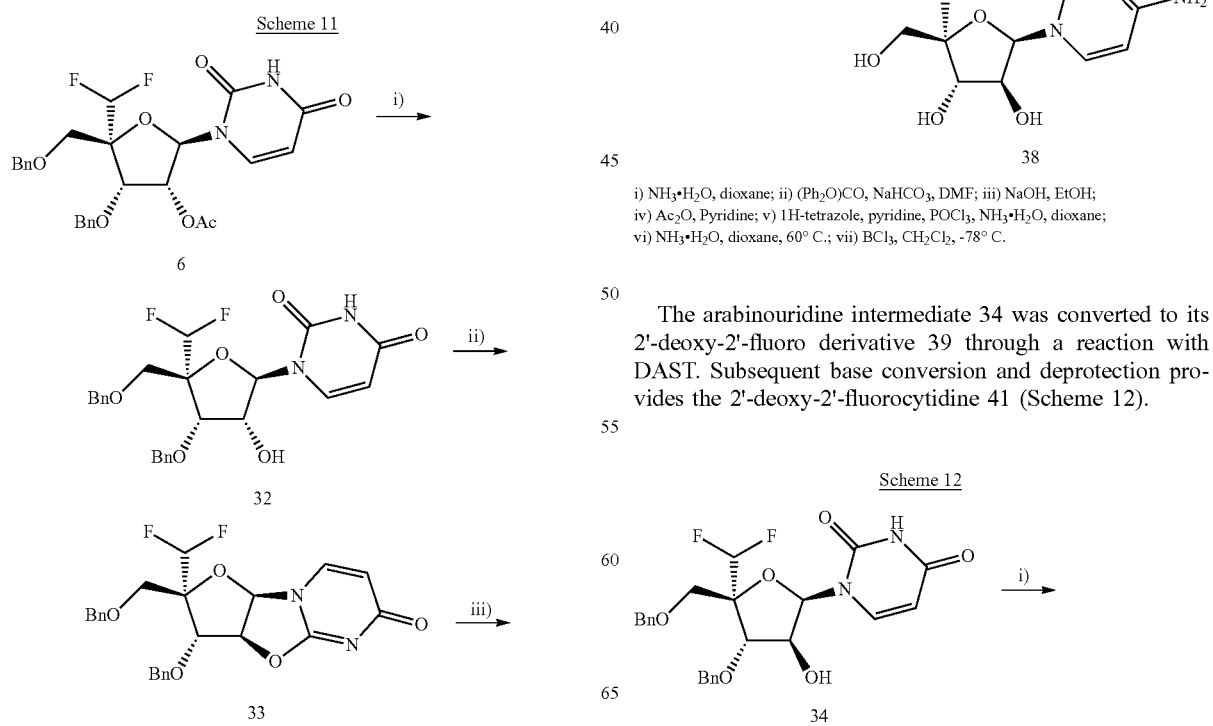

i) NH₃·H₂O, dioxane; ii) (Ph₂O)CO, NaHCO₃, DMF; iii) NaOH, EtOH;
iv) Ac₂O, Pyridine; v) 1H-tetrazole, pyridine, POCl₃, NH₃·H₂O, dioxane;
vi) NH₃·H₂O, dioxane, 60° C.; vii) BCl₃, CH₂Cl₂, -78° C.

The arabinouridine intermediate 34 was converted to its 2'-deoxy-2'-fluoro derivative 39 through a reaction with DAST. Subsequent base conversion and deprotection provides the 2'-deoxy-2'-fluorocytidine 41 (Scheme 12).

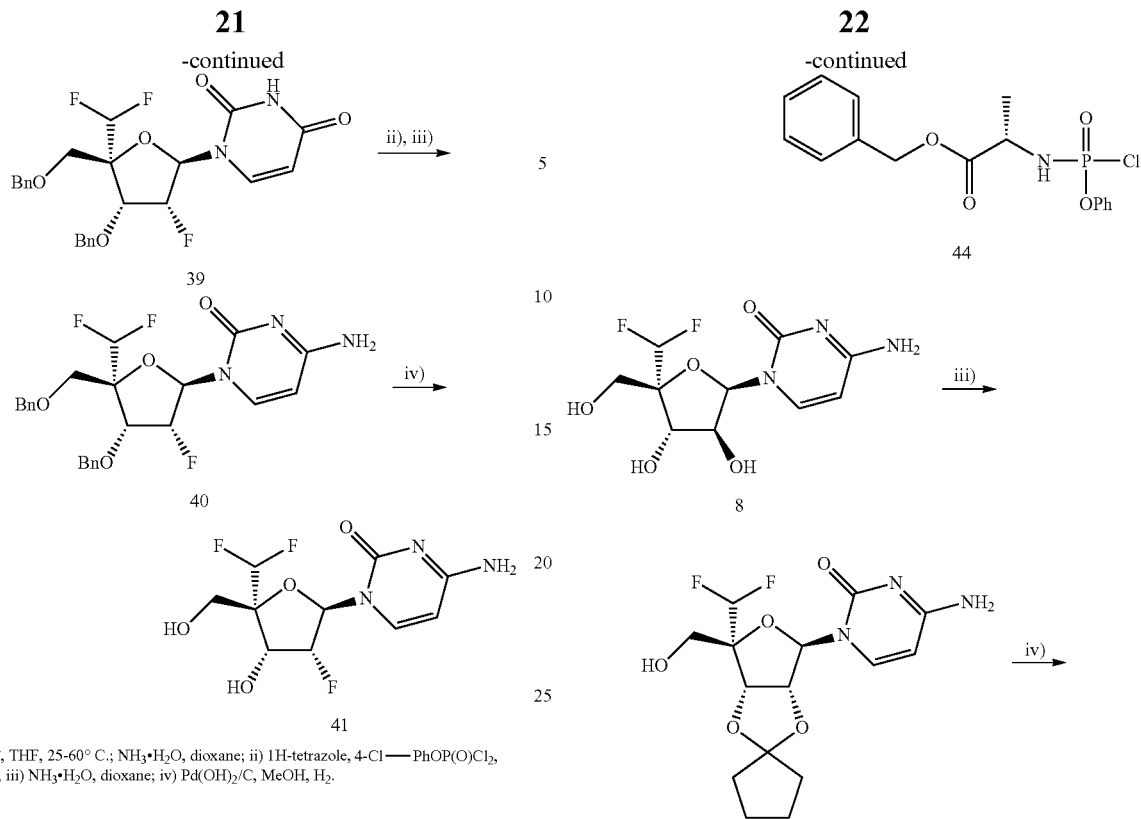

i) DAST, THF, 25-60° C.; NH₃•H₂O, dioxane; ii) 1H-tetrazole, 4-Cl—PhOP(O)Cl₂, pyridine; iii) NH₃•H₂O, dioxane; iv) Pd(OH)₂/C, MeOH, H₂.

The phosphoramidate compound 47 was synthesized following standard coupling methods as shown in Scheme 13. The neopenty ester derivative was synthesized in a similar manner and outlined in Scheme 14.

Scheme 13.

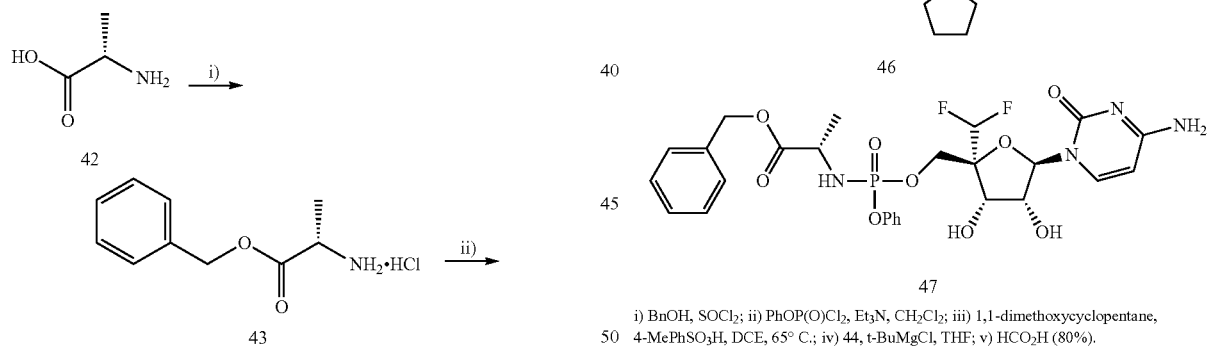

i) BnOH, SOCl₂; ii) PhOP(O)Cl₂, Et₃N, CH₂Cl₂; iii) 1,1-dimethoxycyclopentane, 4-MePhSO₃H, DCE, 65° C.; iv) 44, t-BuMgCl, THF; v) HCO₂H (80%).

Scheme 14.

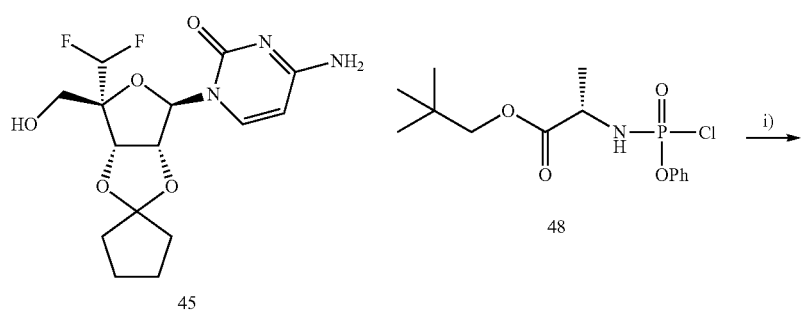

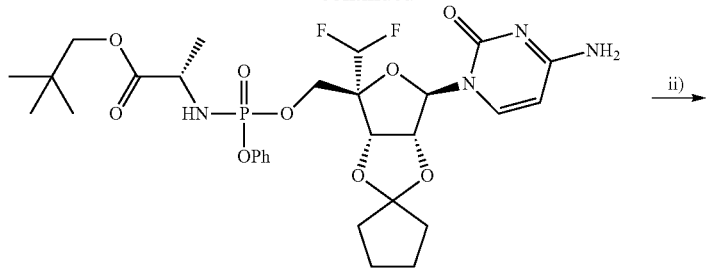

49 ii)

[structure]

50 i) 48, t-BuMgCl, THF; ii) HCO₂H (80%).

General Preparations

Synthesis of compound ((3aR,5R,6S,6aR)-6-(benzyloxy)-5-(benzyloxymethyl)-2,2-dimethyl-tetrahydrofuro[2,3-d][1,3]dioxol-5-yl)methanol (2)

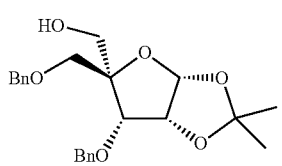

2

To a solution of compound 1 (0.5 g, 1.61 mmol) in dry DMF (20 mL), was added NaH (77.6 mg, 1.94 mmol). After the mixture stirred at room temperature for 0.5 h, BnBr (355 mg, 2.09 mmol) was added drop-wise. The mixture was allowed to stir at r.t. for 4 hrs. TLC (Petroleum ether:Ethyl acetate; 1:3) showed the reaction was complete. The reaction was quenched with water and extracted with ethyl acetate. The organic phase was dried over Na₂SO₄ and then evaporated to dryness under reduced pressure. Purification by silica gel chromatography [ethyl acetate:petroleum ether (1:10 to 1:3)] provided the product 2 (0.42 g, 65%) as a colorless oil. LC-MS (M+H)⁺=401.0

Synthesis of compound (3aR,5R,6S,6aR)-6-(benzyloxy)-5-(benzyloxymethyl)-2,2-dimethyl-tetrahydrofuro[2,3-d][1,3]dioxole-5-carbaldehyde (3)

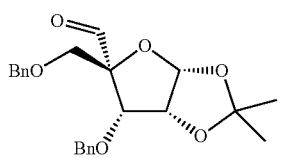

3

DMSO (1.65 mL, 23.6 mmol) was added drop-wise to a cold (−78° C.) solution of oxalyl chloride (1.05 mL, 12.0 mmol) in dichloromethane (50 mL). After stirring for 30 min, a solution of compound 2 (3 g, 7.5 mmol) in dichloromethane (25 mL) was added to the reaction. The stirring was continued for 45 min at −78° C., and triethylamine (3.5 mL, 25.0 mmol) was added to the reaction. The reaction was stirred at −78° C. for 15 min, after which the ice-bath was removed and the reaction was allowed to gradually warm over 45 min. The reaction was diluted with dichloromethane and the organic phase was sequentially washed with 5% aqueous HCl solution, saturated aqueous NaHCO₃ solution, brine, dried (Na₂SO₄) and concentrated under reduced pressure to provide 3 (2.2 g, crude), which was used without any further purification. LC-MS (M+H)⁺=399.1

Synthesis of compound (3aR,5R,6S,6aR)-6-(benzyloxy)-5-(benzyloxymethyl)-5-(difluoromethyl)-2,2-dimethyl-tetrahydrofuro[2,3-d][1,3]dioxole (4)

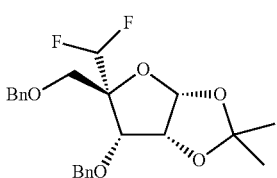

4

To a solution of compound 3 (2.2 g, 5.5 mmol) in dichloromethane (20 mL) was added DAST (4.45 g, 27.6 mmol). The mixture was stirred at room temperature for 14 hrs and then quenched by the addition of saturated NaHCO₃, extracted with EtOAc, dried (Na₂SO₄) and purified by silica gel chromatography [ethyl acetate:petroleum ether (1:10)] to afford 4 (1.0 g, 43%) as an oil. LC-MS (M+H)⁺=421.1

Synthesis of (3R,4S,5R)-4-(benzyloxy)-5-(benzyloxymethyl)-5-(difluoromethyl)-tetrahydrofuran-2,3-diyl diacetate (5)

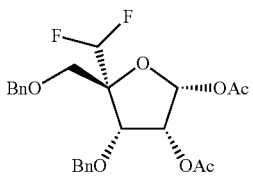

To a solution of compound (3aR,5R,6S,6aR)-6-(benzyloxy)-5-(benzyloxymethyl)-5-(difluoromethyl)-2,2-dimethyl-tetrahydrofuro[2,3-d][1,3]dioxole (1.0 g, 6.3 mmol) in Ac2O (2.5 mL) and AcOH (10 mL) was added H2SO4 (3 drops). The mixture was stirred at room temperature for 3 hrs. TLC showed the reaction was complete. The mixture was poured to water, extracted with EtOAc, dried (Na2SO4) and purified by silica gel chromatography [ethyl acetate:petroleum ether (1:3)] to afford compound 5 (1.0 g, crude) as a light-color oil. LC-MS (M+H)+=465.1

Synthesis of compound (2R,3R,4S,5R)-4-(benzyloxy)-5-(benzyloxymethyl)-5-(difluoromethyl)-2-(2,4-dioxo-3,4-dihydropyrimidin-1 (2H)-yl)-tetrahydrofuran-3-yl acetate (6)

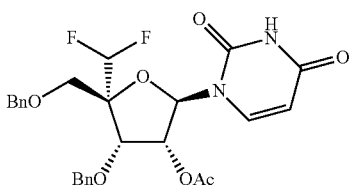

The mixture of uracil (482 mg, 4.32 mmol) and BSA (1.75 g, 8.64 mmol) in MeCN (20 ml) was stirred at room temperature for 3 hrs. Compound 5 (1.0 g, 2.16 mmol) and SnCl4 (2.4 g, 9.3 mmol) was added respective, then stirred at 65° C. for 12 hrs. The mixture was quenched with saturated NaHCO3 solution, extracted with EtOAc (200 mL×3), dried over Na2SO4 and purified by silica gel chromatography [ethyl acetate:petroleum ether (1:10)] to afford the product (450 mg, 40%) as a yellow solid. LC-MS (M+H)+=517.1

Synthesis of compound 1-((2R,3R,4S,5R)-5-(difluoromethyl)-3,4-dihydroxy-5-(hydroxymethyl)-tetrahydrofuran-2-yl)pyrimidine-2,4(1H,3H)-dione (7)

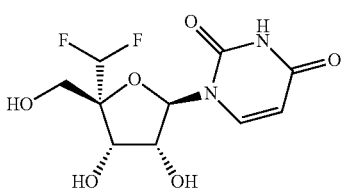

The mixture of compound 1-((2R,3R,4S,5R)-4-(benzyloxy)-5-(benzyloxymethyl)-5-(difluoromethyl)-3-hydroxytetrahydrofuran-2-yl)pyrimidine-2,4(1H,3H)-dione (450 mg 0.87 mmol) in CH3CN (10 mL) was added NH3.H2O (10 mL) stirred at room temperature overnight. The mixture was concentrated and concentrated and dissolved in methanol (30 mL). To this was added Pd(OH)2/C (1.0 g). The reaction mixture was stirred under an atmosphere of hydrogen and at room temperature overnight, the mixture was concentrated and purified by Prep-HPLC to afford 7 (100 mg, 40%) as white solid. LC-MS (M+H)+=295.0

1H NMR (300 MHz, DMSO-d6): δ 11.42 (s, 1H), 7.89-7.86 (d, 1H, J=8.1 Hz), 6.30-5.94 (m, 2H), 5.78-5.64 (m, 2H), 5.56-5.51 (m, 2H), 4.31-4.25 (m, 1H), 4.21-4.18 (m, 1H), 3.75-3.71 (m, 1H), 3.62-3.57 (m, 1H).

Synthesis of compound 4-amino-1-((2R,3R,4S,5R)-5-(difluoromethyl)-3,4-dihydroxy-5-(hydroxymethyl)-tetrahydrofuran-2-yl)pyrimidin-2(1H)-one (8)

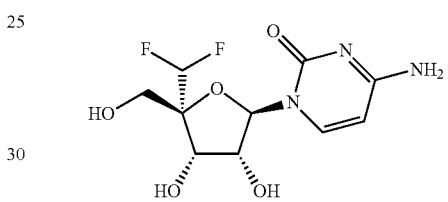

To a solution of 7 (0.1 g, 0.34 mmol) in dry pyridine (15 mL) was added Ac2O (5 mL). The mixture was stirred at room temperature overnight and then evaporated to dryness under reduced pressure. The residue was treated with saturated aqueous NaHCO3 solution extracted with ethyl acetate. The organic phase was separated, dried (Na2SO4) and evaporated to dryness under reduced pressure. Purification by silica gel chromatography [ethyl acetate:petroleum ether (1:10)] gave the acetylated intermediate (0.12 g, 84%) as a white solid. MS [M+H]+=420.1. The acetylated intermediate (0.12 g, 0.286 mmol) and 1H-tetrazole (0.02 g, 0.429 mmol) were azeotroped with pyridine and then dissolved in anhydrous pyridine (20 mL). The solution was cooled by an ice-water bath, and 4-chlorophenylphosphorodichloridate (84 mg, 0.343 mmol) was added. The reaction mixture was stirred at 0-5° C. for 5 min and then allowed to warm to room temperature. After 5 h, the reaction mixture was evaporated to dryness under reduced pressure and the residue was partitioned between CH2Cl2 and saturated aqueous NaHCO3 solution. The organic phase was separated, dried (Na2SO4), and evaporated to dryness under reduced pressure. The crude product was treated with NH3.H2O (10 mL) in 1,4-dioxane (20 mL) for 16 h at room temperature and then evaporated to dryness under reduced pressure. The crude material was dissolved in NH3 in MeOH (7N, 30 mL) and the mixture was stirred for 18 h at room temperature and then evaporated to dryness under reduced pressure. Purification by preparative HPLC column purification gave 8 (51 mg, 61%) as a white solid. MS [M+H]+=294.0

1H NMR (300 MHz, DMSO-d6) δ 7.80-7.78 (d, J=7.8 Hz, 1H), 7.28-7.24 (brs, 2H), 6.28-5.92 (m, 2H), 5.81-5.78 (d, J=7.5 Hz, 1H), 5.53-5.38 (m, 3H), 4.30-4.19 (m, 2H), 3.68-3.60 (m, 2H).

Synthesis of compound (2R,3R,4S,5R)-4-(benzyloxy)-5-(benzyloxymethyl)-5-(difluoromethyl)-2-(2-isobutyramido-6-oxo-1,6-dihydropurin-9-yl)-tetrahydrofuran-3-yl acetate (21)

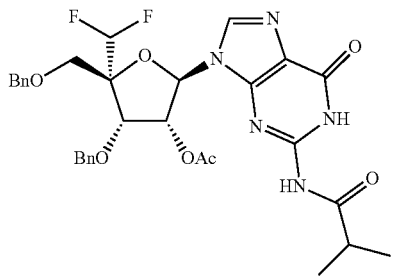

21

To a solution of compound N-(6-oxo-6,9-dihydro-1H-purin-2-yl)isobutyramide (0.57 g, 2.58 mmol) in anhydrous CH$_3$CN (50 mL) was added BSA (1.26 mL, 5.17 mmol) portion-wise while maintaining the reaction temperature at 25° C. Then the reaction was stirred at 40° C. for 1 h until a clear solution persisted. Compound 5 (0.6 g, 1.29 mmol) in CH$_3$CN (5 mL) was added into the mixture at 0° C. followed by TMSOTf (0.94 mL, 5.17 mmol). The mixture was stirred at 40° C. for 2 h and then poured into saturated NaHCO$_3$ solution (10 mL) at 0° C., extracted with ethyl acetate, washed with water, brine solution, dried over Na$_2$SO$_4$ and evaporated to dryness under reduced pressure. The crude compound was purified by silica gel chromatography [petroleum ether:ethyl acetate (5:1 to 1:1)] to provide the product 21 as white foam (0.5 g, 60%). LC-MS: (M+H)$^+$=626

Synthesis of compound 2-amino-9-((2R,3R,4S,5R)-4-(benzyloxy)-5-(benzyloxymethyl)-5-(difluoromethyl)-3-hydroxy-tetrahydrofuran-2-yl)-1H-purin-6(9H)-one (22)

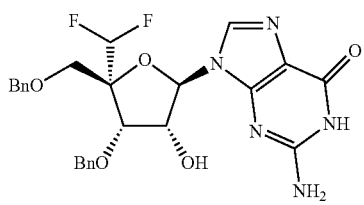

22

A mixture of compound 21 (0.5 g, crude) in NH$_3$.MeOH (7 N, 40 mL) was stirred at 35° C. for 16 h and then evaporated to dryness. Purification by silica gel chromatography [dichloromethane:methanol (100:1 to 20:1)] to give the product 22 as a white foam (0.22 g, 53%). LC-MS (M+H)$^+$=514

Synthesis of compound 2-amino-9-((2R,3R,4S,5R)-5-(difluoromethyl)-3,4-dihydroxy-5-(hydroxymethyl)-tetrahydrofuran-2-yl)-1H-purin-6(9H)-one (23)

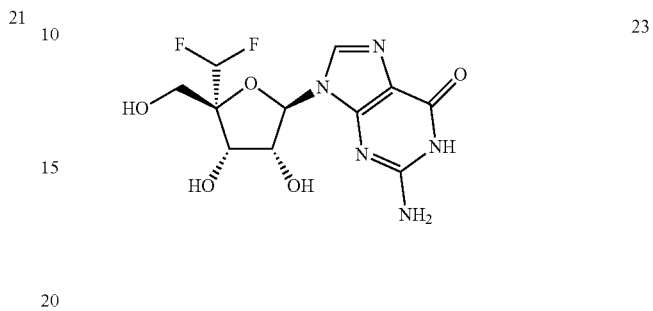

23

To a solution of compound 22 (0.22 g, 0.42 mmol) in methanol (30 mL) was added HCO$_2$NH$_4$ (600 mg, 9.52 mmol), followed by Pd(OH)$_2$/C (500 mg). The reaction mixture was stirred at 80° C. for 15 h, then cooled to 25° C., filtered and then evaporated to dryness under reduced pressure. Purification by silica gel chromatography [dichloromethane:methanol (20:1 to 5:1)] and prep-HPLC provided the product 23 (0.046 g, 33%) as a white solid. LC-MS (M+H)$^+$=334.1

$^1$H NMR (300 MHz, d$_6$-DMSO) δ 10.64 (s, 1 H), 7.93 (s, 1 H), 6.50 (s, 2 H), 6.28-5.92 (dd, J=52.8, 56.4 Hz, 1 H), 5.87-5.83 (d, J=14.7 Hz, 1 H), 5.62-5.45 (m, 3 H), 4.73-4.67 (m, 1 H), 4.27-4.24 (m, 1 H), 3.72-3.58 (m, 2 H).

Synthesis of (2R,3R,4S,5R)-2-(6-benzamido-9H-purin-9-yl)-4-(benzyloxy)-5-(benzyloxymethyl)-5-(difluoromethyl)-tetrahydrofuran-3-yl acetate (25)

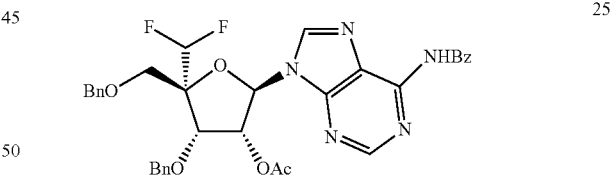

25

To a solution of compound 5 (1.44 g, 6.02 mmol) in anhydrous CH$_3$CN (15 mL) was added BSA (7.2 mL, 30.1 mmol) portion-wise while maintaining the reaction temperature at 25° C. After the reaction mixture became clear, compound 1 (0.4 g, 0.86 mmol) in CH$_3$CN (5 mL) and SnCl$_4$ (0.42 mL, 3.5 mmol) was added into the mixture. The mixture was stirred at 85° C. for 20 h, then it was poured into saturated NaHCO$_3$ (10 mL) at 0° C., extracted with ethyl acetate, the combined organic layer was washed with H$_2$O (100 mL), brine solution (100 mL), dried over Na$_2$SO$_4$ and evaporated to dryness. Purification by silica gel chromatography column [dichloromethane:methanol; (30:1)] to give product 25 as an colorless oil (0.225 g, 25%). LC-MS: (M+H)$^+$=393

Synthesis of (2R,3R,4S,5R)-2-(6-amino-9H-purin-9-yl)-4-(benzyloxy)-5-(benzyloxy methyl)-5-(difluoromethyl)-tetrahydrofuran-3-ol (26)

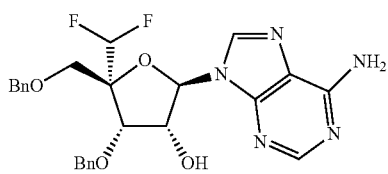

26

A mixture of compound 25 (0.225 g, 0.35 mmol) in NH₃.MeOH (40 mL) was stirred in a sealed tube at 65° C. for 16 hrs, warmed to 25° C. and stirred for 3 hrs. TLC showed the reaction was completed, the reaction solution was concentrated and the crude compound was purified by silica gel chromatography column [dichloromethan:methanol (30:1)] to give product 26 as an colorless oil (0.16 g, 92%).
LC-MS (M+H)⁺=469

Synthesis of (2R,3S,4R,5R)-5-(6-amino-9H-purin-9-yl)-2-(difluoromethyl)-2-(hydroxylmethyl)-tetrahydrofuran-3,4-diol (27)

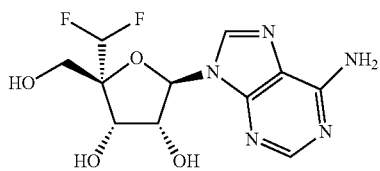

27

Concentrated HCl (37%) 1 drop was added into the mixture of compound 3 (0.048 g, 0.1 mmol) and Pd(OH)₂/C (0.8 g) in MeOH (5 mL), after addition, the whole mixture was stirred at 25° C. under hydrogen atmosphere. After 2 h, the reaction mixture was filtered and evaporated to dryness under reduced pressure. Purification by prep-HPLC afforded 27 (0.024 g, 85%) as a white solid. L-MS (M+H)⁺=318.
¹H NMR (300 MHz, d₆-DMSO) δ 8.52 (s, 1 H), 8.24 (s, 1 H), 6.94 (br s, 2 H), 6.47-6.11 (m, 1 H), 5.99 (d, J=7.8 Hz, 1 H), 5.81-5.79 (m, 2 H), 5.59 (br s, 1 H), 4.46 (br s, 1 H), 4.32 (br s, 1 H), 3.74 (br s, 1 H), and 3.65 (br s, 1 H).

Synthesis of (2R,3R,4S,5R)-2-(4-amino-5-chloro-2-oxopyrimidin-1(2H)-yl)-4-(benzyloxy)-5-(benzyloxymethyl)-5-(difluoromethyl)-tetrahydrofuran-3-yl acetate (29)

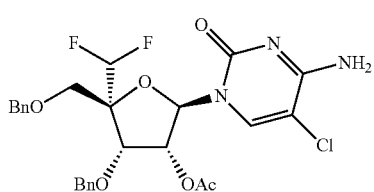

29

To a solution of 4-amino-5-chloropyrimidin-2(1H)-one 28 (0.336 g, 2.33 mmol) in anhydrous CH₃CN (10 mL) was added BSA (0.945 g, 4.64 mmol) portion-wise while maintaining the reaction temperature at 25° C. After the reaction mixture became clear, compound 5 (0.54 g, 1.16 mmol) in CH₃CN (2 mL) and SnCl₄ (1.2 g, 4.64 mmol) was added into the mixture. The mixture was stirred at 65° C. for 1 h, then cooled and poured into saturated NaHCO₃ solution (20 mL). The organic phase was extracted with ethyl acetate, washed with water, brine, dried (Na₂SO₄) and evaporated to dryness under reduced pressure. Purification by flash silica gel chromatography [dichloromethane:methanol (40:1)] gave 29 as a white solid (0.24 g, 31%). LC-MS: (M+H)⁺=550.1

Synthesis of 4-amino-1-((2R,3R,4S,5R)-4-(benzyloxy)-5-(benzyloxymethyl)-5-(difluoromethyl)-3-hydroxy-tetrahydrofuran-2-yl)-5-chloropyrimidin-2(1H)-one (30)

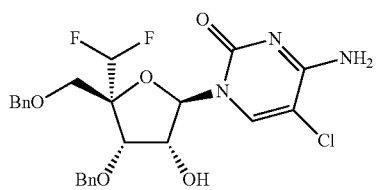

30

A mixture of compound 29 (0.235 g, 0.43 mmol) in NH₃-MeOH (10 mL) was stirred at r.t for 3 h and then evaporated to dryness under reduced pressure. Purification by silica gel chromatography column [dichloromethane:methanol (40:1)] gave 30 as a white solid (0.135 g, 62%). LC-MS: (M+H)⁺=508.1

Synthesis of 4-amino-5-chloro-1-((2R,3R,4S,5R)-5-(difluoromethyl)-3,4-dihydroxy-5-(hydroxymethyl)-tetrahydrofuran-2-yl)pyrimidin-2(1H)-one (31)

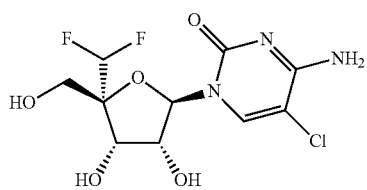

31

BCl₃ (2.46 mL, 2.46 mmol) was added to a cooled (−78° C.) solution of compound 30 (0.125 g, 0.246 mmol) in dry dichloromethane (10 mL). The mixture was cooled to 0° C. and pyridine (0.5 mL) and MeOH (2 mL) were added. The reaction mixture was evaporated to dryness under reduced pressure. Purification by prep-HPLC provided 31 (0.035 g, 44%) as a white solid. LC-MS (M+H)⁺=328.1
¹H NMR (300 MHz, DMSO-d₆) δ 8.12 (s, 1 H), 7.99 (s, 1 H), 7.35 (s, 1 H), 6.27-5.91 (m, 2 H), 5.57 (m, 2 H), 5.44-5.42 (d, J=6.3 Hz, 1 H), 4.25-4.16 (m, 2 H), 3.62 (m, 2 H).

Synthesis of 1-((2R,3R,4S,5R)-4-(benzyloxy)-5-(benzyloxymethyl)-5-(difluoromethyl)-3-hydroxy-tetrahydrofuran-2-yl)pyrimidine-2,4(1H,3H)-dione (32)

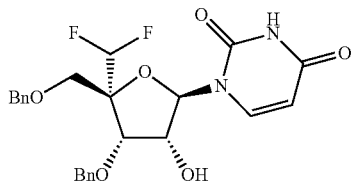

32

A solution of compound 6 (0.52 g, 1 mmol) in NH$_3$-MeOH/dioxane (6 mL/6 mL) was stirred at 20° C. After 18 h the reaction mixture was evaporated to dryness under reduced pressure. Purification by silica gel chromatography [petroleum ether:ethyl acetate (4:1 to 1.5:1)] provided 32 (0.314 g, 61%) as a white solid.
LC-MS: (M+H)$^+$=475.1

Synthesis of 2,2'-anhydro-4'-difluoromethyl-1-(β-arabinofuranosyl)uracil (33)

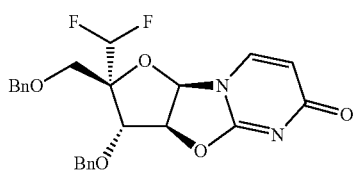

33

Diphenyl carbonate (0.258 g, 1.2 mmol) and sodium hydrogen carbonate (0.184 g, 2.2 mmol) were added to a solution of 32 (0.52 g, 1.1 mmol) in dry DMF (10 mL). The reaction mixture was stirred at 110° C. for 2 h, then cooled and evaporated to dryness under reduced pressure. The residue was dissolved with dichloromethane and washed with water, brine, dried (Na$_2$SO$_4$) and then evaporated to dryness under reduced pressure to give the crude product 33 (0.45 g) as a white solid, which was used directly without further purification. LC-MS: (M+H)$^+$=457.2

Synthesis of 1-((2R,3S,4S,5R)-4-(benzyloxy)-5-(benzyloxymethyl)-5-(difluoromethyl)-3-hydroxy-tetrahydrofuran-2-yl)pyrimidine-2,4(1H,3H)-dione (34)

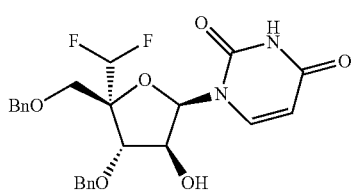

34

A solution of aqueous NaOH (1N, 5 mL) was added to a solution of compound 33 (0.45 g) in ethanol (10 mL). After stirring at 20° C. for 3 h, the reaction mixture was adjusted to pH=7 by strong-acid cation-exchange resin, filtered and evaporated to dryness under reduced pressure. Purification by silica gel chromatography [dichlormethane:methanol (40:1)] provided 34 (0.12 g, 25%) as a white solid. LC-MS: (M+H)$^+$=475.2

Synthesis of (2R,3S,4S,5R)-4-(benzyloxy)-5-(benzyloxymethyl)-5-(difluoromethyl)-2-(2,4-dioxo-3,4-dihydropyrimidin-1(2H)-yl)-tetrahydrofuran-3-yl acetate (35)

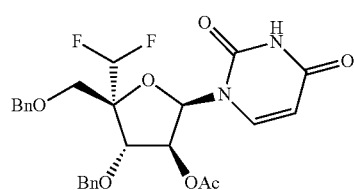

35

Ac$_2$O (0.5 mL) was added into a solution of compound 34 (0.114 g, 0.24 mmol) in dry pyridine (4 mL). The reaction mixture was stirred at 20° C. for 3 h and then quenched by saturated aqueous NaHCO$_3$ solution (2 mL). The organic phase was extracted with dichloromethane and then evaporated to dryness under reduced pressure. Purification by silica gel chromatography [petroleum ether:ethyl acetate (4:1)] afforded 35 (0.12 g, 88%) as a white solid. LC-MS: (M+H)$^+$=517.2

Synthesis of (2R,3S,4S,5R)-2-(4-amino-2-oxopyrimidin-1(2H)-yl)-4-(benzyloxy)-5-(benzyloxymethyl)-5-(difluoromethyl)-tetrahydrofuran-3-yl acetate (36)

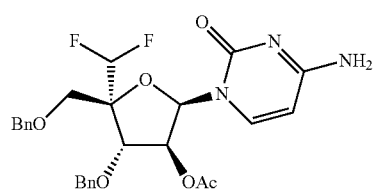

36

4-Chlorophenylphosphonic dichloride (0.4 g, 0.81 mmol) was added to a cooled (0° C.) solution of 1-H-tetrazole (0.056 g, 0.81 mmol) and 35 (0.113 g, 0.22 mmol) in dry pyridine (5 mL). The reaction mixture was left to stir under a nitrogen atmosphere at 20° C. for 3 h and then evaporated to dryness under reduced pressure. The residue was dissolved in dioxane and NH$_3$.H$_2$O (5 mL) was added. After stirring for 5 h at 20° C., the reaction mixture was evaporated to dryness under reduced pressure to afford 36 (0.2 g, crude).

Synthesis of 4-amino-1-((2R,3S,4S,5R)-4-(benzy-loxy)-5-(benzyloxymethyl)-5-(difluoromethyl)-3-hydroxy-tetrahydrofuran-2-yl)pyrimidin-2(1H)-one (37)

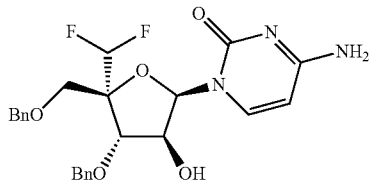

A solution of compound 36 (0.112 g, 0.21 mmol) in NH$_3$.MeOH (4 mL) was stirred at 60° C. for 12 h and then cooled and evaporated to dryness under reduced pressure to give 37 as a white solid. LC-MS: (M+H)$^+$=474.2

Synthesis of 4-amino-1-((2R,3S,4S,5R)-5-(difluoromethyl)-3,4-dihydroxy-5-(hydroxymethyl)-tetrahydrofuran-2-yl)pyrimidin-2(1H)-one (38)

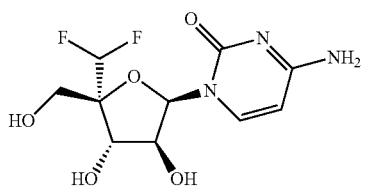

BCl$_3$ (3.7 mL, 3.7 mmol) was added to a solution of compound 37 (0.175 g, 0.37 mmol) in dichloromethane (10 mL) cooled to −78° C. The reaction was stirred at −78° C. for 3 h, then warmed to 25° C. and stirred for a further 12 h. The reaction mixture was cooled to 0° C. and then pyridine was added into the mixture, followed by methanol. The reaction mixture was evaporated to dryness under reduced pressure. Purification by prep-HPLC afforded the product 38 (0.052 g, 41%) as a white solid. LC-MS (M+H)$^+$=294.1

$^1$H NMR (300 MHz, DMSO-d$_6$) δ 7.59-7.56 (d, J=7.5 Hz, 1 H), 7.13-7.06 (d, J=21.3 Hz, 2 H), 6.24-6.23 (d, J=5.7 Hz, 1 H), 6.07 (s, 1 H), 5.92-5.90 (d, J=5.1 Hz, 1 H), 5.67-5.62 (m, 2 H), 5.41-5.38 (m, 1 H), 4.30-4.28 (m, 1 H), 4.15-4.14 (m, 1 H), 3.64-3.59 (m, 2 H).

Synthesis of compound 1-((2R,3R,4R,5R)-4-(benzyloxy)-5-(benzyloxymethyl)-5-(difluoromethyl)-3-fluoro-tetrahydrofuran-2-yl)pyrimidine-2,4(1H,3H)-dione (39)

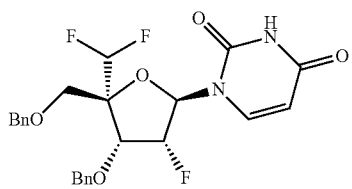

Diethylaminosulfur trifluoride (7.6 g, 47.4 mmol) was added to a suspension of compound 34 (1.5 g, 3.16 mmol) in dry THF (150 mL). The mixture was stirred at 60° C. for 16 h and then cooled to room temperature. The mixture was quenched by the addition of saturated aqueous NaHCO$_3$ solution and then extracted with ethyl acetate. The organic phase was washed with brine, dried (Na$_2$SO$_4$) and evaporated to dryness under reduced pressure. Purification by silica gel chromatography [petroleum ether:ethyl acetate (4:1)] afforded 39 as a brown solid (700 mg, 46%). LC-MS (M+H)$^+$=477.4

Synthesis of compound 4-amino-1-((2R,3R,4R,5R)-4-(benzyloxy)-5-(benzyloxymethyl)-5-(difluoromethyl)-3-fluoro-tetrahydrofuran-2-yl)pyrimidin-2(1H)-one (40)

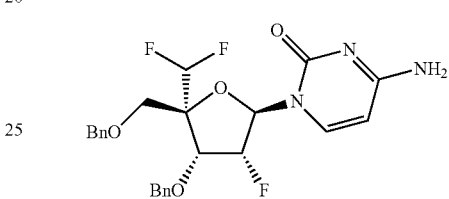

4-Chlorophenyl phosphorodichloridate (0.68 g, 2.77 mmol) was added to a solution of compound 39 (0.22 g, 0.462 mmol) and 1-H-tetrazole (0.485 g, 6.93 mmol) in dry pyridine (100 mL) at 0° C. After stirring at room temperature for 3 h, the reaction mixture was evaporated to dryness under reduced pressure. The residue was dissolved in dichloromethane and washed with saturated aqueous NaHCO$_3$ solution, brine, dried (Na$_2$SO$_4$) and evaporated to dryness under reduced pressure. Purification by silica gel chromatography (petroleum ether:ethyl acetate (4:1)] provided the intermediate as an red oil. The intermediate was dissolved in dioxane (40 mL) and NH$_3$.H$_2$O (2 mL) was added. After stirring for 30 min, the reaction mixture was evaporated to dryness under reduced pressure. Purification by silica gel chromatography [dichloromethane:methanol (10:1)] provided 40 as a brown solid (180 mg, 81%).

LC-MS (M+H)$^+$=476.1

Synthesis of compound 4-amino-1-((2R,3R,4R,5R)-5-(difluoromethyl)-3-fluoro-4-hydroxy-5-(hydroxymethyl)-tetrahydrofuran-2-yl)pyrimidin-2(1H)-one (41)

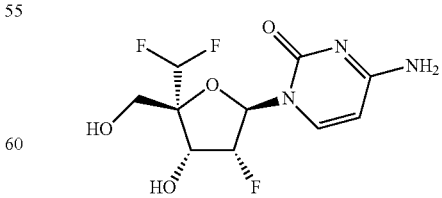

A mixture of compound 40 (160 mg, 0.34 mmol), Pd(OH)$_2$/C (0.8 g) and concentrated aqueous HCl (2 drops, 37%) in methanol (10 mL) was stirred under an atmosphere of hydrogen for 10 min, filtered and evaporated to dryness under reduced pressure. Purification by preparative HPLC afforded 41 as a white solid (26 mg, 25%). LC-MS (M+H)$^+$=296.1

$^1$H NMR (300 MHz, d$_6$-DMSO) δ 7.79 (d, J=7.2 Hz, 1 H), 7.33 (d, J=10.4 Hz, 2 H), 6.26-5.99 (m, 3 H), 5.77 (d, J=7.6 Hz, 1 H), 5.44 (t, J=5.2 Hz, 1 H), 5.15 (dt, J$_1$=53.6 Hz, J$_2$=5.2 Hz, 1 H), 4.58-4.53 (m, 1 H), 3.70-3.58 (m, 2 H).

Synthesis of (S)-1-(benzyloxy)-1-oxopropan-2-aminium chloride (43)

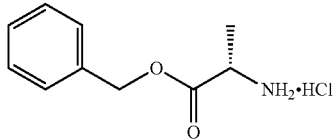

43

Thionyl chloride (27 mL) was added drop-wise to a solution L-alanine (42) (6.83 g, 76.6 mmol) in benzyl alcohol (120 mL). After stirring at 0° C. for 2 h, the reaction mixture was warmed to room temperature and stirred for a further 24 h and then evaporated to dryness under reduced pressure. Trituration with diethyl ether, followed by filtration and evaporation under reduced pressure, provided the crude product 43 (3.5 g), which was used directly without further purification. LC-MS (M-Cl)$^+$=180

Synthesis of (2S)-benzyl 2-(chloro(phenoxy)phosphorylamino)propanoate (44)

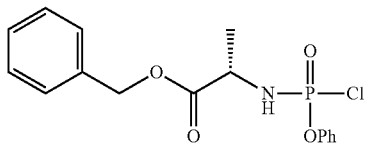

44

Phenyl phosphorodichloridate (1.17 g, 2 N) was added to a solution of 43 (1 g, 5.58 mmol) in dichloromethane at –78° C. Triethylamine (1.13 g, 11.173 mmol) was then added drop-wise. Once complete, the reaction mixture was allowed to warm to room temperature and then evaporated to dryness under reduced pressure. Purification by silica gel chromatography [petroleum ether:ethyl acetate (3:1)] provided 44 as an colorless oil (1.2 g, 60%). LC-MS (M+H)$^+$=354

Synthesis of Compound (45)

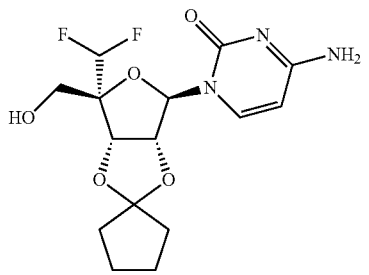

45

To a mixture of compound 8 (0.11 g, 0.375 mmol) and compound 1,1-dimethoxycyclopentane (0.495 g, 3.8 mmol) in dichloromethane was added PTSA (0.01 g). The resulting mixture was stirred at 65° C. for 1 h and then evaporated to dryness under reduced pressure. Purification by silica gel chromatography [dichloromethane:methanol (10:1)] afforded 45 as a white solid (0.17 g, 90%). LC-MS (M+H)$^+$=360.2

Synthesis of Compound (46)

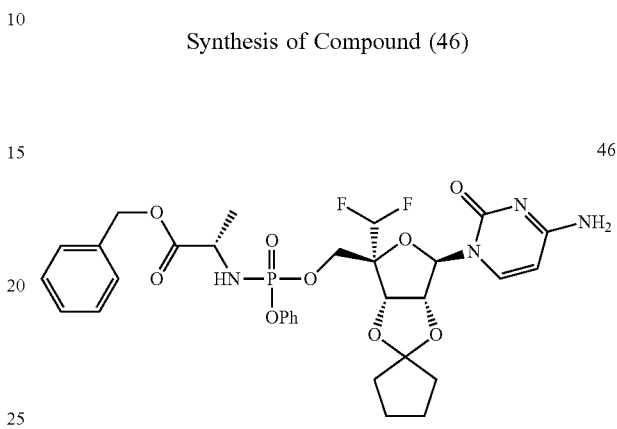

46

To a suspension of compound 45 (0.08 g, 0.223 mmol) in dry THF was added t-BuMgBr (1.3 mL, 1.34 mmol) at 0° C. under nitrogen atmosphere, then warmed to 25° C. and stirred for 30 min. The reaction mixture was then cooled to 0° C. and then (2S)-Benzyl 2-(chloro(phenoxy)phosphorylamino)propanoate (0.236 g, 0.668 mmol) was added drop-wise. The reaction mixture was stirred at room temperature for 2 h and then quenched by the addition of methanol (1 mL). The mixture was then evaporated to dryness under reduced pressure. Purification by silica gel chromatography [dichloromethane:methanol (10:1)] afforded 46 as a white solid (0.19 g). LC-MS (M+H)$^+$=677.1

Synthesis of compound (S)-benzyl 2-((((2R,3S,4R,5R)-5-(4-amino-2-oxopyrimidin-1(2H)-yl)-2-(difluoromethyl)-3,4-dihydroxy-tetrahydrofuran-2-yl)methoxy)(phenoxy)phosphorylamino)propanoate (47)

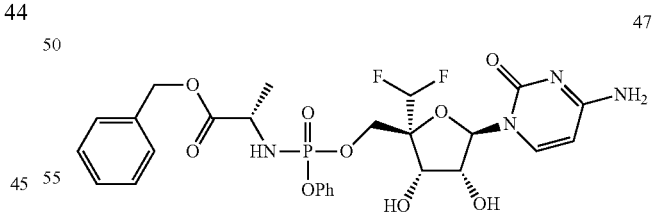

47

A solution of compound 46 (0.18 g, 0.26 mmol) in formic acid (80%, v/v) was stirred at 25° C. for 18 h and then evaporated to dryness under reduced pressure. Purification by prep-HPLC provided 47 as a white solid (12.8 mg, 5%). LC-MS (M+H)$^+$=611.1

$^1$H NMR (300 MHz, DMSO-d$_6$) δ 7.55-7.16 (m, 13 H), 6.33-5.97 (m, 3 H), 5.78-5.77 (m, 2 H), 5.47-5.46 (m, 1 H), 5.15-5.06 (m, 2 H), 4.23-3.95 (m, 5 H), 1.28-1.23 (t, J=7.5 Hz, 3 H).

Synthesis of Compound (49)

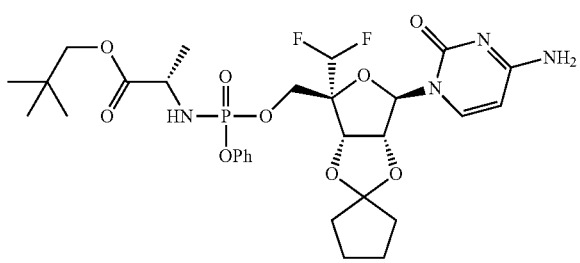

To a suspension of compound 45 (0.2 g, 0.5 mmol) in dry THF was added t-BuMgBr (3 mL, 3 mmol) at 0° C. under nitrogen atmosphere, then warmed to 25° C. and stirred for 30 min, compound (2S)-neopentyl 2-(chloro(phenoxy)phosphorylamino)propanoate (0.5 g, 1.5 mmol) was added drop wise at 0° C. over 10 min, after addition, the whole mixture was stirred at 25° C. After 2 hrs, the reaction mixture was quenched with 1 mL MeOH and then evaporated to dryness under reduced pressure. Purification by silica gel chromatography [dichloromethane:methanol (20:1 to 15:1)], provided 49 as a white solid (0.3 g, crude). LC-MS (M+H)$^+$=657

Synthesis of compound (S)-neopentyl 2-((((2R,3S,4R,5R)-5-(4-amino-2-oxopyrimidin-1(2H)-yl)-2-(difluoromethyl)-3,4-dihydroxy-tetrahydrofuran-2-yl)methoxy)(phenoxy)phosphorylamino)propanoate (50)

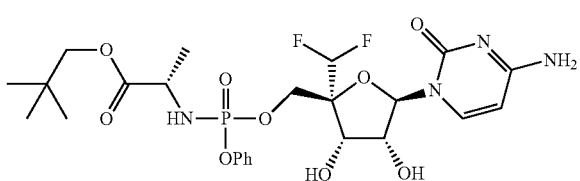

A solution of compound 49 (0.3 g, crude) in HCOOH (80%, v/v, 30 mL) was stirred at room temperature. After 12 h the reaction mixture was cooled to 0° C. and neutralized with 1M aqueous NaHCO3 solution. The organic phase was extracted with ethyl acetate, washed with water, brine solution, dried (Na2SO4) and evaporated to dryness under reduced pressure. Purification by prep-HPLC provided 50 (17 mg, 9.8%) as a white solid. LC-MS (M+H)$^+$=590.9

$^1$H NMR (300 MHz, DMSO-d$_6$) δ 7.54-7.18 (m, 8 H), 6.32-6.06 (m, 3 H), 5.81-5.65 (m, 2 H), 5.48-5.46 (m, 1 H), 4.24-4.12 (m, 4 H), 3.95-3.89 (dd, 1 H), 3.79-3.69 (m, 2 H), 1.29-1.24 (m, 3 H), 0.88 (s, 9 H).

Biological Examples

Influenza Assay

This assay measures the ability of the active compounds derived from the compounds of formula I to inhibit the essential influenza RNA polymerase. The influenza polymerase was obtained from purified influenza virus particles and the rate of nucleotide incorporation was measured from the quantitation of a radiolabeled nucleotide tracer during the polymerase reaction.

Metabolism Assay

This assay measures the ability of human cells to generate the active compounds from the compounds of formula I. The active compounds are the triphosphate (TP) derivatives of the nucleoside analogs. The assay is determining the concentration of specific nucleoside triphosphates formed in human cells exposed to compounds of formula I after methanol extraction of cells and analysis of soluble nucleoside triphosphate using LC-MS.

TABLE 1

Activity of nucleotide triphosphates in influenza polymerase assay.

| Compound Number | Structure | Activity IC$_{50}$ μM |
|---|---|---|
| TPP-1 | 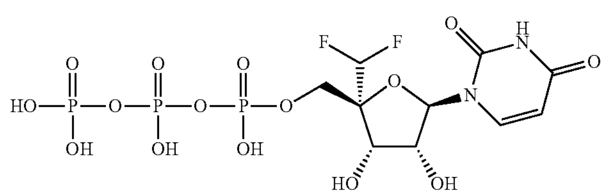 [SMILES: O=c1ccn([C@@H]2O[C@@](COP(=O)(O)OP(=O)(O)OP(=O)(O)O)(C(F)F)[C@@H](O)[C@H]2O)c(=O)[nH]1] | B |
| TPP-2 | 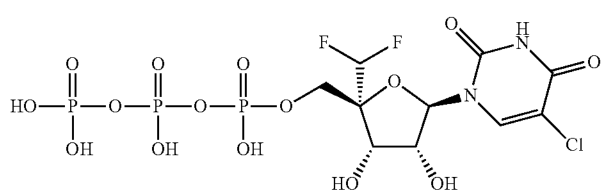 [SMILES: O=c1[nH]c(=O)n([C@@H]2O[C@@](COP(=O)(O)OP(=O)(O)OP(=O)(O)O)(C(F)F)[C@@H](O)[C@H]2O)cc1Cl] | B |

TABLE 1-continued

Activity of nucleotide triphosphates in influenza polymerase assay.

| Compound Number | Structure | Activity IC$_{50}$ μM |
|---|---|---|
| TPP-3 | 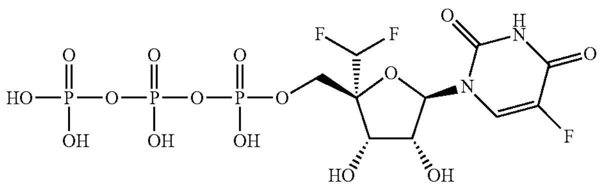 [SMILES: O=c1[nH]c(=O)n([C@@H]2O[C@@](COP(=O)(O)OP(=O)(O)OP(=O)(O)O)(C(F)F)[C@@H](O)[C@H]2O)cc1F] | B |
| TPP-4 | 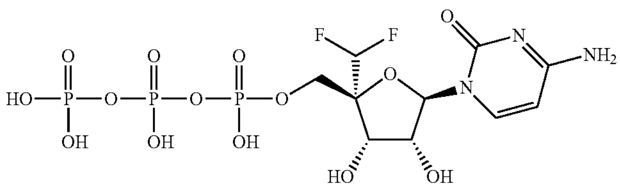 [SMILES: Nc1ccn([C@@H]2O[C@@](COP(=O)(O)OP(=O)(O)OP(=O)(O)O)(C(F)F)[C@@H](O)[C@H]2O)c(=O)n1] | A |
| TPP-5 | 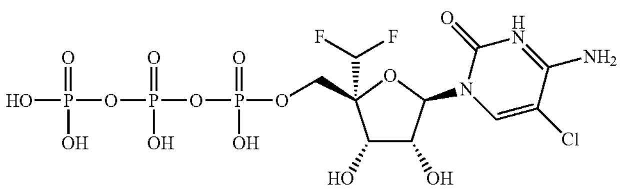 | B |
| TPP-6 | 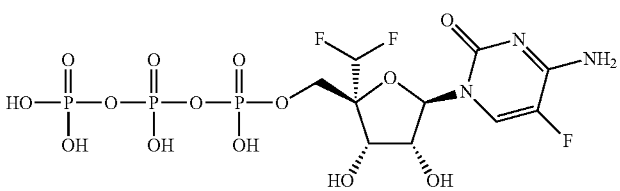 [SMILES: Nc1nc(=O)n([C@@H]2O[C@@](COP(=O)(O)OP(=O)(O)OP(=O)(O)O)(C(F)F)[C@@H](O)[C@H]2O)cc1F] | A |
| TPP-7 | 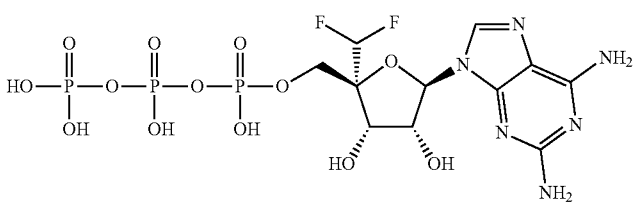 [SMILES: Nc1nc(N)c2ncn([C@@H]3O[C@@](COP(=O)(O)OP(=O)(O)OP(=O)(O)O)(C(F)F)[C@@H](O)[C@H]3O)c2n1] | C |
| TPP-8 | 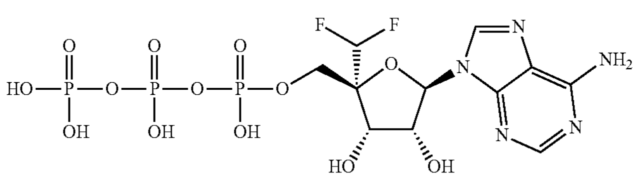 [SMILES: Nc1ncnc2c1ncn2[C@@H]1O[C@@](COP(=O)(O)OP(=O)(O)OP(=O)(O)O)(C(F)F)[C@@H](O)[C@H]1O] | A |
| TPP-9 | 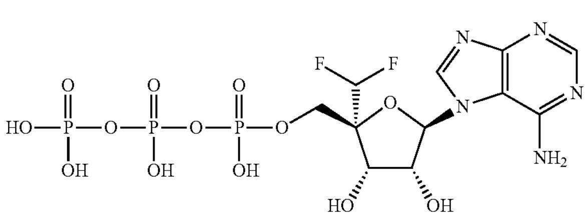 [SMILES: Nc1ncnc2ncn([C@@H]3O[C@@](COP(=O)(O)OP(=O)(O)OP(=O)(O)O)(C(F)F)[C@@H](O)[C@H]3O)c12] | A |

TABLE 1-continued

Activity of nucleotide triphosphates in influenza polymerase assay.

| Compound Number | Structure | Activity $IC_{50}$ µM |
|---|---|---|
| TPP-10 | (triphosphate-CHF$_2$-ribose-deazaguanine nucleoside structure) | A |

Activity in influenza polymerase assay is as follows: A = $IC_{50}$ < 10 µM; B = $IC_{50}$ 10-100 µM; C = $IC_{50}$ > 100 µM Dosage and Administration As shown in above Table the compounds of formula I have the potential to be efficacious as antiviral drugs for the treatment of influenza infections in humans, or are metabolized to a compound that exhibit such activity.

In another embodiment of the invention, the active compound or its prodrug derivative or salt can be administered in combination with another antiviral agent, such as an anti-influenza agent or an immunomodulatory compound, including those of formula I. When the active compound or its derivative or salt are administered in combination with another antiviral or immunomodulatory agent the activity may be increased over the parent compound. This can easily be assessed by preparing the derivative and testing its anti-influenza activity according to the method described herein.

Administration of the active compound may range from continuous (intravenous drip) to several or single administrations per day (for example, Q.I.D) or less frequent administrations and may include oral, topical parenteral, intramuscular, intravenous, subcutaneous, transdermal (which may include a penetration enhancement agent), buccal and suppository administration, among other routes of administration.

The 4'-difluoromethyl substituted nucleoside derivatives as well as their pharmaceutically useable salts, can be used as medicaments in the form of any pharmaceutical formulation. The pharmaceutical formulation can be administered enterally, either orally, e.g. in the form of tablets, coated tablets, dragées, hard and soft gelatine capsules, solutions, emulsions, syrups, or suspensions, or rectally, e.g. in the form of suppositories. They can also be administered parenterally (intramuscularly, intravenously, subcutaneously or intrasternal injection or infusion techniques), e.g. in the form of injection solutions, nasally, e.g. in the form of nasal sprays, or inhalation spray, topically and so forth.

For the manufacture of pharmaceutical preparations, the 4'-substituted nucleoside derivatives, as well as their pharmaceutically useable salts, can be formulated with a therapeutically inert, inorganic or organic excipient for the production of tablets, coated tablets, dragées, hard and soft gelatine capsules, solutions, emulsions or suspensions.

The compounds of formula I can be formulated in admixture with a pharmaceutically acceptable carrier. For example, the compounds of the present invention can be administered orally as pharmacologically acceptable salts. Because the compounds of the present invention are mostly water soluble, they can be administered intravenously in physiological saline solution (e.g., buffered to a pH of about 7.2 to 7.5). Conventional buffers such as phosphates, bicarbonates or citrates can be used for this purpose. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulation, esterification, etc.) which are well within the ordinary skill in the art. It is also well within the ordinary skill of the art to modify the route of administration and dosage regimen of a particular compound in order to manage the pharmacokinetics of the present compounds for maximum beneficial effect in patients.

For parenteral formulations, the carrier will usually comprise sterile water or aqueous sodium chloride solution, though other ingredients including those which aid dispersion may be included. Of course, where sterile water is to be used and maintained as sterile, the compositions and carriers must also be sterilized. Injectable suspensions may also be prepared, in which case appropriate liquid carriers, suspending agents and the like may be employed.

Suitable excipients for tablets, coated tablets, dragées, and hard gelatin capsules are, for example, lactose, corn starch and derivatives thereof, talc, and stearic acid or its salts.

If desired, the tablets or capsules may be enteric-coated or sustained release by standard techniques.

Suitable excipients for soft gelatine capsules are, for example, vegetable oils, waxes, fats, semi-solid and liquid polyols.

Suitable excipients for injection solutions are, for example, water, saline, alcohols, polyols, glycerin or vegetable oils.

Suitable excipients for suppositories are, for example, natural and hardened oils, waxes, fats, semi-liquid or liquid polyols.

Suitable excipients for solutions and syrups for enteral use are, for example, water, polyols, saccharose, invert sugar and glucose.

The pharmaceutical preparations of the present invention may also be provided as sustained release formulations or other appropriate formulations.

The pharmaceutical preparations can also contain preservatives, solubilizers, stabilizers, wetting agents, emulsifiers, sweeteners, colorants, flavourants, salts for adjustment of the osmotic pressure, buffers, masking agents or antioxidants.

The pharmaceutical preparations may also contain other therapeutically active agents known in the art.

The dosage can vary within wide limits and will, of course, be adjusted to the individual requirements in each particular case. For oral administration, a daily dosage of between about 0.01 and about 100 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 100 mg/kg body weight per day. A typical preparation will contain from about 5% to about 95% active compound (w/w). The daily dosage can be administered as a single dosage or in divided dosages, typically between 1 and 5 dosages per day.

In certain pharmaceutical dosage forms, the pro-drug form of the compounds, especially including acylated (acetylated or other) derivatives, pyridine esters and various salt forms of the present compounds are preferred. One of ordinary skill in the art will recognize how to readily modify the present compounds to pro-drug forms to facilitate delivery of active compounds to a target site within the host organism or patient. One of ordinary skill in the art will also take advantage of favorable pharmacokinetic parameters of the pro-drug forms, where applicable, in delivering the present compounds to targeted site within the host organism or patient to maximize the intended effect of the compound.

Indications and Method of Treatment

The application provides a method for treating a Influenza infection comprising administering to a patient in need thereof a therapeutically effective amount of a compound of Formula I.

The application provides the above method, further comprising administering an immune system modulator or one or more antiviral agents that inhibits replication of Influenza, or a combination thereof.

The application provides the above method for inhibiting replication of Influenza in a cell comprising administering a compound of Formula I.

Combination Therapy

The compounds of the invention and their isomeric forms and pharmaceutically acceptable salts thereof are useful in treating and preventing influenza infection alone or when used in combination with other compounds targeting viral or cellular elements or functions involved in the influenza lifecycle. Classes of compounds useful in the invention include, without limitation, all classes of influenza antivirals.

The present invention is not limited to the aforementioned classes or compounds and contemplates known and new compounds and combinations of biologically active agents. It is intended that combination therapies of the present invention include any chemically compatible combination of a compound of this inventive group with other compounds of the inventive group or other compounds outside of the inventive group, as long as the combination does not eliminate the anti-viral activity of the compound of this inventive group or the anti-viral activity of the pharmaceutical composition itself.

Combination therapy can be sequential, that is treatment with one agent first and then a second agent (for example, where each treatment comprises a different compound of the invention or where one treatment comprises a compound of the invention and the other comprises one or more biologically active agents) or it can be treatment with both agents at the same time (concurrently). Sequential therapy can include a reasonable time after the completion of the first therapy before beginning the second therapy. Treatment with both agents at the same time can be in the same daily dose or in separate doses. Combination therapy need not be limited to two agents and may include three or more agents. The dosages for both concurrent and sequential combination therapy will depend on absorption, distribution, metabolism and excretion rates of the components of the combination therapy as well as other factors known to one of skill in the art. Dosage values will also vary with the severity of the condition to be alleviated. It is to be further understood that for any particular subject, specific dosage regimens and schedules may be adjusted over time according to the individual's need and the judgment of the one skilled in the art administering or supervising the administration of the combination therapy.

It will be understood that references herein to treatment extend to prophylaxis as well as to the treatment of existing conditions, and that the treatment of animals includes the treatment of humans as well as other mammals. Furthermore, treatment of an Influenza infection, as used herein, also includes treatment or prophylaxis of a disease or a condition associated with or mediated by Influenza infection, or the clinical symptoms thereof.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:
1. A compound of Formula I

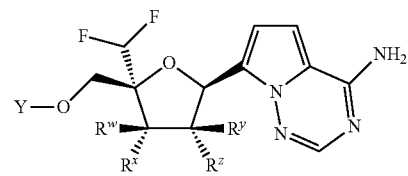

wherein:
Y is H or P(=X)(R')(R);
R is O—$R^1$ or $NHR^{1'}$;
  $R^{1'}$ is —C($R^{2a}$)($R^{2b}$)C(=O)$OR^3$;
R' is N($R^4$)C($R^{2a}$)($R^{2b}$)C(=O)$OR^3$, —OP(=O)(OH)OP(=O)(OH)OH, or —$OR^3$;
  $R^1$ is H, lower haloalkyl, or aryl, wherein aryl is phenyl or naphthylenyl, optionally substituted with one or more lower alkyl, lower alkenyl, lower alkynyl, lower alkoxy, halo, lower haloalkyl, —N($R^{1a}$)$_2$, acylamino, —SO$_2$N($R^{1a}$)$_2$, —C(=O)$R^{1b}$, —SO$_2$($R^{1c}$), —NHSO$_2$($R^{1c}$), nitro, cyano, or $R^{1"}$;

each $R^{1a}$ is independently H or lower alkyl;
each $R^{1b}$ is independently —O$R^{1a}$ or —N($R^{1a}$)$_2$;
each $R^{1c}$ is lower alkyl;
each $R^{2a}$ and $R^{2b}$ is independently H, lower alkyl, —(CH$_2$)$_r$N($R^{1a}$)$_2$, lower hydroxyalkyl, —CH$_2$SH, —(CH$_2$)S(O)$_p$Me, —(CH$_2$)$_n$NHC(=NH)NH$_2$, (1H-indol-3-yl)methyl, (1H-indol-4-yl)methyl, —(CH2)$_m$C(=O)$R^{1b}$, aryl and aryl lower alkyl, wherein aryl is optionally substituted with one or more hydroxy, lower alkyl, lower alkoxy, halo, nitro or cyano;
m is 0, 1, or 2;
n is 1, 2, or 3;
p is 1 or 2;
r is 1 or 2;
or $R^{2a}$ is H and $R^{2b}$ and $R^4$ together form (CH$_2$)$_n$;
each $R^3$ is independently H, lower alkyl, lower haloalkyl, phenyl or phenyl lower alkyl, wherein phenyl and phenyl lower alkyl are optionally substituted with lower alkoxy;
or one $R^3$ and $R^{1"}$ together form CH$_2$;
each $R^4$ is independently H, lower alkyl;
or $R^{2b}$ and $R^4$ together form (CH$_2$)$_3$;
$R^w$, $R^y$, and $R^z$ are each independently H, OH or F;
$R^x$ is H, OH, or F;
or one $R^3$ and $R^x$ together form a bond;
or $R^1$ and $R^x$ together form a bond; and
X is O or S;
or a pharmacologically acceptable salt thereof.

2. The compound of claim 1, wherein $R^W$ is H, $R^y$ is H, $R^x$ is OH, and $R^z$ is OH.

3. The compound of claim 1, wherein $R^W$ is H, $R^y$ is OH, $R^x$ is OH, and $R^z$ is H.

4. The compound of claim 1, wherein $R^W$ is H, $R^y$ is F, $R^x$ is OH, and $R^z$ is H.

5. The compound of claim 1, wherein $R^W$ is H, $R^y$ is OH, $R^x$ is OH, and $R^z$ is H.

6. The compound of claim 1, wherein X is O.

7. The compound of claim 1, wherein X is S.

8. The compound of claim 1, wherein R is O—$R^1$, and $R^1$ is naphthylenyl.

9. The compound of claim 1, wherein R' is N($R^4$)C($R^{2a}$)($R^{2b}$)C(=O)O$R^3$, $R^4$ is H, $R^{2a}$ is H, $R^{2b}$ is methyl, and $R^3$ is isopropyl.

10. A method of treating Influenza comprising administering to a patient in need thereof a therapeutically effective amount of the compound of claim 1.

11. A composition comprising the compound of claim 1, admixed with at least one carrier, diluent or excipient.

12. A composition comprising the compound of claim 1 in combination with one or more antiviral compounds.

13. A composition comprising the compound of claim 1 in combination with one or more anti-Influenza compounds.

14. A composition comprising the compound of claim 1 in combination with one or more antiviral compounds, admixed with at least one carrier, diluent or excipient.

15. A composition comprising the compound of claim 1 in combination with one or more anti-Influenza compounds, admixed with at least one carrier, diluent or excipient.

16. A method of treating a viral infection comprising administering to a patient in need thereof a therapeutically effective amount of the compound of claim 1.

17. A method for treating an Influenza infection comprising administering to a patient in need thereof a therapeutically effective amount of a compound of Formula I

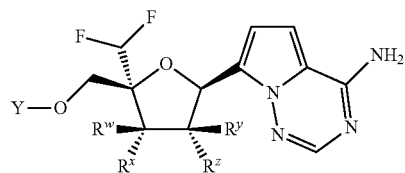

I wherein:
Y is H or P(=X)(R')(R);
R is O—$R^1$ or NH$R^{1'}$;
$R^{1'}$ is —C($R^{2a}$)($R^{2b}$)C(=O)O$R^3$;
R' is N($R^4$)C($R^{2a}$)($R^{2b}$)C(=O)O$R^3$, —OP(=O)(OH)OP(=O)(OH)OH, or —O$R^3$;
$R^1$ is H, lower haloalkyl, or aryl, wherein aryl is phenyl or naphthylenyl, optionally substituted with one or more lower alkyl, lower alkenyl, lower alkynyl, lower alkoxy, halo, lower haloalkyl, —N($R^{1a}$)$_2$, acylamino, —SO$_2$N($R^{1a}$)$_2$, —C(=O)$R^{1b}$, —SO$_2$($R^{1c}$), —NHSO$_2$($R^{1c}$), nitro, cyano, or $R^{1"}$;
each $R^{1a}$ is independently H or lower alkyl;
each $R^{1b}$ is independently —O$R^{1a}$ or —N($R^{1a}$)$_2$;
each $R^{1c}$ is lower alkyl;
each $R^{2a}$ and $R^{2b}$ is independently H, lower alkyl, —(CH$_2$)$_r$N($R^{1a}$)$_2$, lower hydroxyalkyl, —CH$_2$SH, —(CH$_2$)S(O)$_p$Me, —(CH$_2$)$_n$NHC(=NH)NH$_2$, (1H-indol-3-yl)methyl, (1H-indol-4-yl)methyl, —(CH2)$_m$C(=O)$R^{1b}$, aryl and aryl lower alkyl, wherein aryl is optionally substituted with one or more hydroxy, lower alkyl, lower alkoxy, halo, nitro or cyano;
m is 0, 1, or 2;
n is 1, 2, or 3;
p is 1 or 2;
r is 1 or 2;
or $R^{2a}$ is H and $R^{2b}$ and $R^4$ together form (CH$_2$)$_n$;
each $R^3$ is independently H, lower alkyl, lower haloalkyl, phenyl or phenyl lower alkyl, wherein phenyl and phenyl lower alkyl are optionally substituted with lower alkoxy;
or one $R^3$ and $R^{1"}$ together form CH$_2$;
each $R^4$ is independently H, lower alkyl;
or $R^{2b}$ and $R^4$ together form (CH$_2$)$_3$;
$R^w$, $R^y$, and $R^z$ are each independently H, OH or F;
$R^x$ is H, OH, or F;
or one $R^3$ and $R^x$ together form a bond;
or $R^1$ and $R^x$ together form a bond; and
X is O or S;
or a pharmacologically acceptable salt thereof.

18. A compound of claim 1, wherein the compound of formula I is selected from the group consisting of:
(2R,3S,4R,5S)-5-(4-aminopyrrolo[2,1-f][1,2,4]triazin-7-yl)-2-(difluoromethyl)-2-(hydroxymethyl)tetrahydrofuran-3,4-diol;
(2R,3R,4R,5S)-5-(4-aminopyrrolo[2,1-f][1,2,4]triazin-7-yl)-2-(difluoromethyl)-4-fluoro-2-(hydroxymethyl)tetrahydrofuran-3-ol;
(2R,3S,4S,5S)-5-(4-aminopyrrolo[2,1-f][1,2,4]triazin-7-yl)-2-(difluoromethyl)-2-(hydroxymethyl)tetrahydrofuran-3,4-diol; and (2R,3R,4S,5S)-5-(4-aminopyrrolo[2,1-f][1,2,4]triazin-7-yl)-2-(difluoromethyl)-4-fluoro-2-(hydroxymethyl)tetrahydrofuran-3-ol.

19. A method for treating an Influenza infection comprising administering to a patient in need thereof a therapeutically effective amount of the compound of claim 18.

\* \* \* \* \*